US012579646B2

(12) United States Patent
Nachit et al.

(10) Patent No.: US 12,579,646 B2
(45) Date of Patent: Mar. 17, 2026

(54) SYSTEM AND METHOD FOR DETERMINING A RISK OF HAVING OR DEVELOPING STEATOHEPATITIS AND/OR A COMPLICATION THEREOF

(71) Applicant: UNIVERSITÉ CATHOLIQUE DE LOUVAIN, Louvain-la-neuve (BE)

(72) Inventors: Maxime Nachit, Louvain-la-neuve (BE); Isabelle Leclercq, Louvain-la-neuve (BE)

(73) Assignee: UNIVERSITÉ CATHOLIQUE DE LOUVAIN, Louvain-la-Neuve (BE)

( * ) Notice: Subject to any disclaimer, the term of this patent is extended or adjusted under 35 U.S.C. 154(b) by 48 days.

(21) Appl. No.: 18/567,565

(22) PCT Filed: Jun. 9, 2022

(86) PCT No.: PCT/EP2022/065769
§ 371 (c)(1),
(2) Date: Dec. 6, 2023

(87) PCT Pub. No.: WO2022/258788
PCT Pub. Date: Dec. 15, 2022

(65) Prior Publication Data
US 2024/0281965 A1 Aug. 22, 2024

(30) Foreign Application Priority Data

Jun. 9, 2021 (EP) ..................................... 21178620

(51) Int. Cl.
*G06T 7/00* (2017.01)
*G16H 50/30* (2018.01)

(52) U.S. Cl.
CPC ........... *G06T 7/0012* (2013.01); *G16H 50/30* (2018.01); *G06T 2207/10081* (2013.01);
(Continued)

(58) Field of Classification Search
None
See application file for complete search history.

(56) References Cited

U.S. PATENT DOCUMENTS 10,359,435 B2 7/2019 Nikrad et al.
2014/0330106 A1 11/2014 Banerjee et al.
(Continued)

FOREIGN PATENT DOCUMENTS

WO 2014049131 A1 4/2014

OTHER PUBLICATIONS

Tanaka et al., "Relationship between nonalcoholic fatty liver disease and muscle quality as well as quantity evaluated by computed tomography", Liver Int., vol. 40, Issue 1, pp. 120-130, Jan. 2020. (Year: 2020).*
(Continued)

*Primary Examiner* — Katherine L Fernandez
(74) *Attorney, Agent, or Firm* — Workman Nydegger

(57) ABSTRACT
A computer-implemented method for determining a risk of having or developing steatohepatitis and/or a complication thereof in a subject. The method includes the steps of: receiving at least one image of the subject and at least one clinical and/or biological data, both previously obtained from the subject; calculating a score of fat infiltration heterogeneity on the at least one image based on at least one radiomic feature obtained for a region of interest including at least one skeletal muscle; combining the calculated score of fat infiltration heterogeneity with the at least one clinical and/or biological data previously obtained from the subject; determining a risk for the subject of having or developing steatohepatitis and/or a complication thereof based on the combination of the calculated score of fat infiltration heterogeneity with the at least one clinical and/or biological data.

21 Claims, 19 Drawing Sheets

(52) U.S. Cl.
   CPC .............. *G06T 2207/10088* (2013.01); *G06T 2207/10132* (2013.01); *G06T 2207/20081* (2013.01); *G06T 2207/30056* (2013.01)

(56) References Cited

U.S. PATENT DOCUMENTS

| | | | | |
|---|---|---|---|---|
| 2018/0075600 | A1* | 3/2018 | Cales | G06T 7/90 |
| 2018/0099001 | A1* | 4/2018 | Schentag | G01N 33/6893 |
| 2020/0378991 | A1* | 12/2020 | Jia | A61P 1/16 |
| 2021/0209757 | A1* | 7/2021 | Min | A61K 49/04 |

OTHER PUBLICATIONS

International Search Report issued on Aug. 29, 2022, in corresponding International Patent Application No. PCT/EP2022/065769, 4 pages.

Written Opinion of the International Searching Authority issued Aug. 29, 2022, in corresponding International Patent Application No. PCT/EP2022/065769, 9 pages.

"Understanding Your FibroScan Results", Memorial Sloan Kettering Cancer Center, Feb. 27, 2018, XP055865302, URL: https://www.mskcc.org/cancer-care/patient-education/understanding-your-fibroscan-results, 4 pages.

Nachit et al., "A dynamic association between myosteatosis and liver stiffness: Results from a prospective interventional study in obese patients", JHEP Reports, vol. 3, No. 4, Aug. 1, 2021, XP55951979, ISSN: 2589-5559, 10 pages.

Chalsani et al., The Diagnosis and Management of Non-alcoholic Fatty Liver Disease Practice Guideline by the American Gastroenterological Association, American Association for the Stud of Liver Diseases, and American College of Gastroenterology, AGA Institute, Gastroenterology, http://dx.doi.org/10.1053/j.gastro.2012.04.001, Jun. 2012, vol. 142, pp. 1592-1609.

* cited by examiner

| | | NAFLD (n=72) | NAFL (n=34) | NASH (n=38) |
|---|---|---|---|---|
| Age (years) | | 57 ± 14 | 54 ± 16 | 60 ± 13 |
| Sex | Female | 25 | 14 | 11 |
| | Male | 47 | 20 | 27 |
| Steatosis score | 1 | 40 | 24 | 16 |
| | 2 | 15 | 7 | 8 |
| | 3 | 17 | 3 | 14 |
| Activity score | 0 | 23 | 26 | 0 |
| | 1 | 8 | 8 | 0 |
| | 2 | 23 | 0 | 23 |
| | 3 | 13 | 0 | 13 |
| | 4 | 2 | 0 | 2 |
| Fibrosis score | 0 | 25 | 25 | 0 |
| | 1 | 15 | 6 | 9 |
| | 2 | 7 | 2 | 5 |
| | 3 | 11 | 0 | 11 |
| | 4 | 14 | 1 | 13 |
| Tumor | No focal lesion | 27 | 5 | 22 |
| | Benign | 16 | 15 | 1 |
| | HCC | 20 | 7 | 13 |
| | CCC | 1 | 0 | 1 |
| | Metastasis | 8 | 7 | 1 |
| | Total Cancer | 29 | 14 | 15 |

FIG. 3

| | No HCC | HCC | Mean difference | p value |
|---|---|---|---|---|
| Age (years) | 53 ± 14 | 67 ± 9 | N/A | <0.001 |
| Subcutaneous fat area (cm²) | 271 ± 115 | 234 ± 106 | ~ 14% | 0.216 |
| Visceral fat area (cm²) | 202 ± 109 | 266 ± 117 | + 32% | 0.033 |
| Total fat area (cm²) | 473 ± 157 | 500 ± 155 | + 6% | 0.515 |
| PDFF (%) : Psoas | 3.6 ± 2.5 | 4.0 ± 2.0 | + 11% | 0.529 |
| PDFF (%) : Quadratus Lumborum | 3.0 ± 2.2 | 4.7 ± 3.6 | + 58% | 0.021 |
| PDFF (%) : Erector Spinae | 5.7 ± 3.0 | 9.6 ± 5.5 | + 69% | <0.001 |
| PDFF (%) : Oblique | 9.3 ± 5.5 | 10.6 ± 6.6 | + 14% | 0.409 |
| PDFF (%) : Rectus | 8.1 ± 7.0 | 7.2 ± 5.7 | ~ 11% | 0.657 |

FIG. 4

| Variables | NAFLD (n=72) | |
| --- | --- | --- |
| | p value | Beta coefficient |
| Age | 0.003 | 0.42 |
| Sex | 0.036 | - 0.26 |
| Activity score (A1-4) | 0.528 | 0.10 |
| Fibrosis score (F1-4) | 0.608 | - 0.08 |
| Visceral Fat area (cm²) | 0.787 | 0.27 |
| HCC presence | 0.014 | 0.29 |
| Linear multiple regression of Erector Spinae PDFF prediction | | |

FIG. 5

| Variables | NAFLD (n=72) | | | | NASH (n=38) | | | |
|---|---|---|---|---|---|---|---|---|
| | p value of HCC prediction for ES_PDFF | Odds ratio per unit increase (95% CI) | Odds ratio per SD increase (95% CI) | AUROC (95% CI) | p value of HCC prediction for ES_PDFF | Odds ratio per unit increase (95% CI) | Odds ratio per SD increase (95% CI) | AUROC (95% CI) |
| Unadjusted | 0.002 | 1.27 (1.09 – 1.48) | 2.75 (1.46 – 5.2) | 0.72 (0.57 – 0.86) | 0.006 | 1.35 (1.09 – 1.68) | 3.61 (1.45 – 9.00) | 0.79 (0.63 – 0.96) |
| Sex, age adjusted | 0.045 | 1.19 (1.00 – 1.41) | 2.08 (1.02 – 4.26) | 0.84 (0.73 – 0.94) | 0.046 | 1.52 (1.01 – 2.30) | 5.88 (1.03 – 33.56) | 0.93 (0.85 – 1.00) |
| Multivariate model 1 | 0.041 | 1.19 (1.01 – 1.41) | 2.09 (1.03 – 4.25) | 0.84 (0.73 – 0.94) | 0.030 | 1.62 (1.05 – 2.51) | 7.78 (1.22 – 49.61) | 0.94 (0.87 – 1.00) |
| Multivariate model 2 | 0.046 | 1.19 (1.00 – 1.40) | 2.06 (1.01 – 4.20) | 0.84 (0.73 – 0.95) | 0.030 | 1.62 (1.05 – 2.51) | 7.78 (1.22 – 49.61) | 0.94 (0.87 – 1.00) |
| Multivariate model 3 | 0.045 | 1.19 (1.00 – 1.40) | 2.08 (1.02 – 4.26) | 0.84 (0.73 – 0.95) | 0.037 | 1.58 (1.03 – 2.44) | 6.98 (1.12 – 43.43) | 0.94 (0.87 – 1.00) |

Multivariate model 1 was adjusted for age, sex and visceral fat area
Multivariate model 2 was adjusted to NASH activity (A0-1 vs A2+) in addition to factors included in model 1
Multivariate model 3 was adjusted for histological fibrosis stage (F0-1 vs F2+) in addition to factors included in model 1

FIG. 6

Virtual muscle biopsy     Complete muscle ROIs

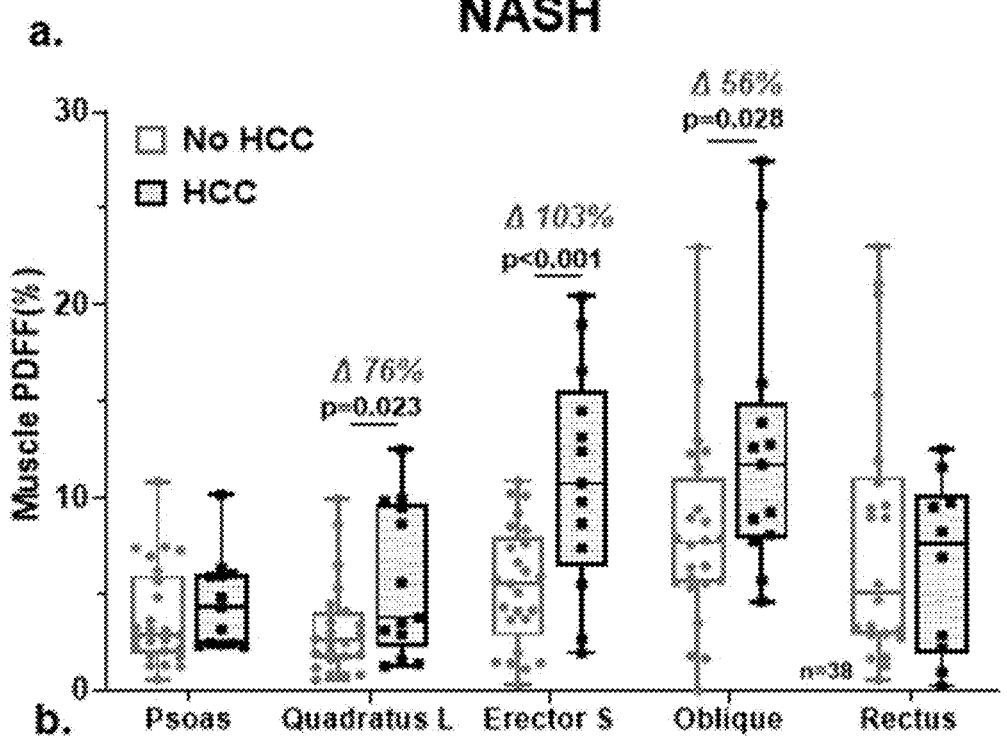
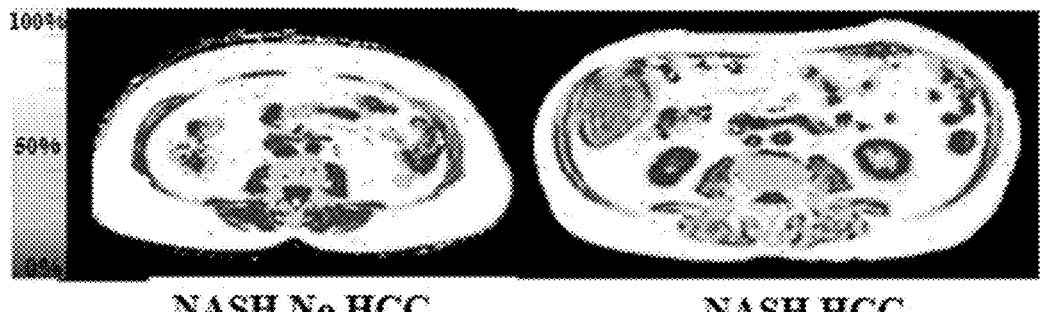
NASH No HCC                    NASH HCC
FIG. 8

| | | HCC in NAFLD (n=20) | Chi-squared test |
|---|---|---|---|
| Fibrosis score | 0 | 4 | |
| | 1 | 4 | |
| | 2 | 2 | p=0.44 |
| | 3 | 4 | |
| | 4 | 6 | |

FIG. 10

| | (A) No focal lesion (n=27) | (B) Benign (n=16) | (C) HCC (n=20) | (D) CCC (n=1) | (E) Meta (n=8) | p value |
|---|---|---|---|---|---|---|
| PDFF (%) : Psoas | 4.1 ± 2.7 | 3.2 ± 2.3 | 4.0 ± 2.1 | / | 3.1 ± 2.2 | N.S. |
| PDFF (%) : Quadratus L. | 3.4 ± 2.7 | 1.9 ± 1.1 | 4.7 ± 3.7 | / | 3.3 ± 1.3 | B vs C = 0.046 |
| PDFF (%) : Erector Spinae | 6.1 ± 3.4 | 5.3 ± 3.0 | 9.6 ± 5.5 | / | 5.0 ± 1.8 | A vs C = 0.028<br>B vs C = 0.028<br>C vs E = 0.060 |
| PDFF (%) : Oblique | 8.3 ± 5.0 | 9.5 ± 6.0 | 10.6 ± 6.6 | / | 10.1 ± 4.8 | N.S. |
| PDFF (%) : Rectus | 7.7 ± 6.5 | 8.1 ± 7.8 | 7.2 ± 5.7 | / | 7.5 ± 7.1 | N.S. |

Multiple comparison using one-way ANOVA followed by Benjamini-Horcberg post-hoc, with p value <0.1 denoted in full and p value >0.1 denoted as N.S.

Abbreviation: HCC, hepatocellular carcinoma; CCC, cholangiocarcinoma; Meta, metastasis.

NB: CCC were excluded since n=1

FIG. 11

| Erector spinae PDFF | | No HCC | HCC | Odds ratio (95% CI) | Relative risk (95% CI) | p value |
|---|---|---|---|---|---|---|
| Optimal Sensitivity<br>Se: 0.85 (0.60 – 0.97)<br>Sp: 0.46 (0.28 – 0.65) | <5.3% | 12 | 2 | 5.1 (0.9 – 25.6) | 1.6 (1.0 – 2.4) | p=0.0773 |
| | ≥5.3% | 13 | 11 | | | |
| Youden index<br>Se: 0.69 (0.42 – 0.87)<br>Sp: 0.84 (0.65 – 0.93) | <8.6% | 21 | 4 | 11.8 (2.2 – 54.8) | 2.7 (1.4 – 6.7) | p=0.0028 |
| | ≥8.6% | 4 | 9 | | | |
| Optimal specificity<br>Se: 0.54 (0.29 – 0.77)<br>Sp: 0.96 (0.81 – 1.00) | <10.5% | 24 | 6 | 28.0 (3.2 – 323.9) | 6.4 (1.7 –35.9) | p=0.0009 |
| | ≥10.5% | 1 | 7 | | | |

Sensitivity and specificity, Odds ratio and Relative Risk computed with Wilson/Brown, Baptista-Pike and Koopman asymptotic score methods, respectively.
p value computed with Fischer's exact test.

FIG. 12

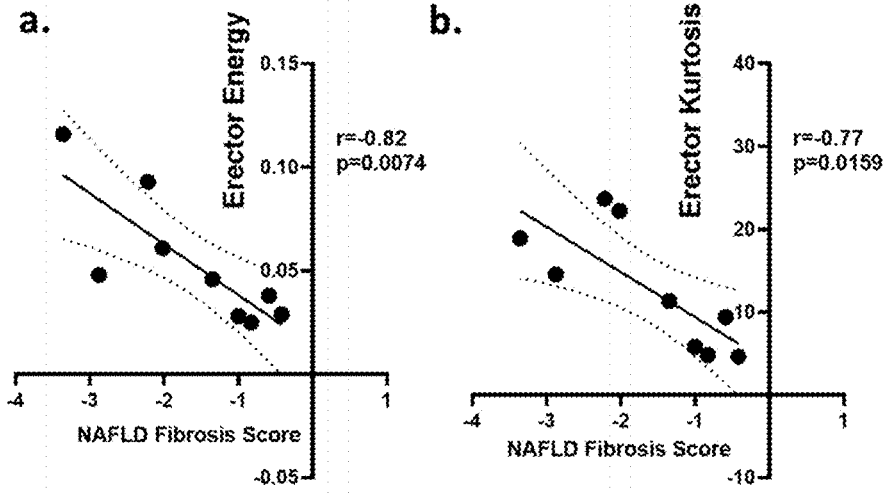
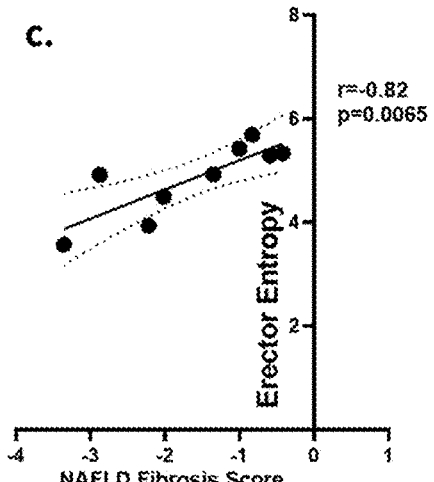
FIG. 18

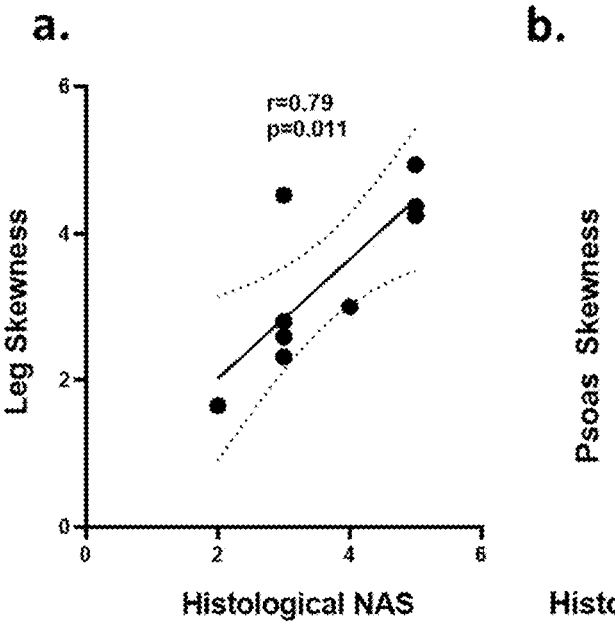
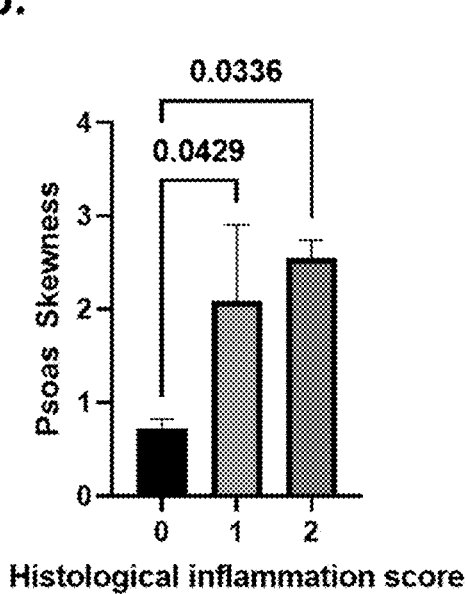
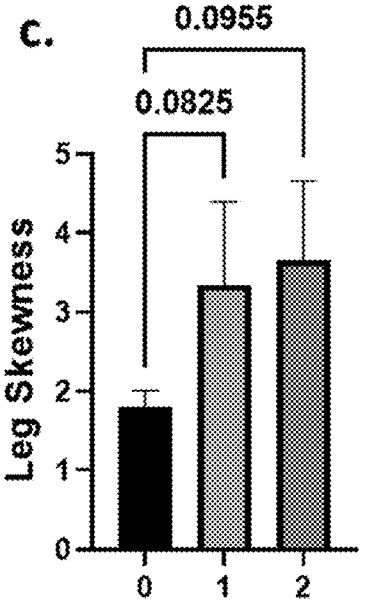
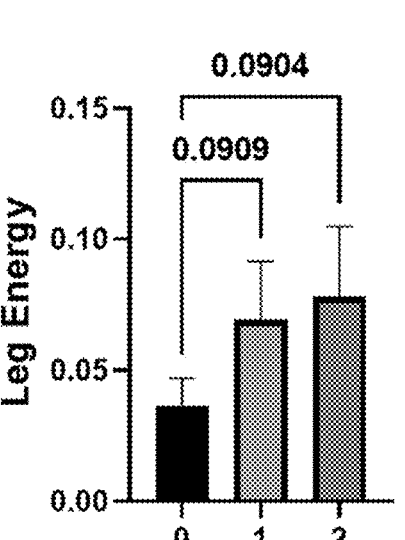
FIG. 19

SYSTEM AND METHOD FOR DETERMINING A RISK OF HAVING OR DEVELOPING STEATOHEPATITIS AND/OR A COMPLICATION THEREOF

FIELD

The present invention pertains to the field of diagnosis in hepatology and more precisely to the diagnosis of steatohepatitis and/or a complication thereof in a subject. In particular, the invention relates to devices and methods for determining a risk of having or developing steatohepatitis through image processing.

BACKGROUND

Steatohepatitis is an aggressive form of fatty liver disease, which is notably included in the non-alcoholic fatty liver disease (NAFLD) spectrum. Steatohepatitis, in particular non-alcoholic steatohepatitis (NASH) has the inherent propensity to progress towards liver fibrosis which can produce progressive liver scarring and lead to cirrhosis or towards hepatocellular carcinoma (liver cancer).

NAFLD is characterized by the presence of hepatic steatosis, i.e., the accumulation of lipids within hepatocytes, said steatosis developing in the absence of use of steatogenic medication or hereditary disorders or inborn error of metabolism. NAFLD is composed of two subtypes of pathologies: fatty liver (NAFL) and NASH. In NAFL, fatty liver disease is characterized by the presence of fat in the liver but with few or no inflammation or liver damage. In NASH, in addition to hepatic steatosis, inflammation with hepatocyte injury (ballooning) is present with or without liver fibrosis (Chalasani N et al., Gastroenterology 2012; 142:1592-609).

Liver cancer is the most common type of primary liver cancer in adults and it is the second leading cause of cancer-related death worldwide. Hepatocellular carcinoma (HCC) accounts for 70-85% of all liver cancers. NAFLD the most prevalent chronic liver disease in the world, is an established risk factor for HCC development. The prevalence of NAFLD-associated HCC is alarmingly increasing. A study conducted in Newcastle (United Kingdom) reported an over ten-fold increase of NAFLD-associated HCC between 2000 and 2010. By 2030, HCC incidence is projected to rise by 137% in the United States with approximately 20% of these new cases related to NAFLD. Hence, tools to evaluate the risk for HCC development in NAFLD patients are urgently needed to optimize surveillance in this vast at-risk population.

NAFLD, NASH and HCC are generally diagnosed through the histological examination by an expert liver pathologist of a liver sample obtained by a biopsy. While liver biopsy is still considered the gold standard to assess the presence and/or the severity of a liver condition in a subject, it does have limitations, notably due to a poor inter- or intra-observer reproducibility and a possible sample bias linked to the small size of the sample. Furthermore, liver biopsy is an invasive medical procedure and as such remains associated with a risk of complication and a significant cost. Therefore, there remains a need for a non-invasive method to specifically and accurately assess the presence of steatohepatitis, in particular NASH, and/or a complication thereof in a subject. In particular, such a non-invasive method would represent a convenient and practical manner to assess the presence of steatohepatitis, in particular NASH, and/or a complication thereof in a subject, to monitor patients suffering from NAFLD or NASH for the development of NASH complications and to monitor treatment response in a subject treated for NASH.

SUMMARY

The present invention relates to a computer-implemented method for determining a risk of having or developing steatohepatitis and/or a complication thereof in a subject, said method comprising the steps of:

receiving at least one image of the subject previously obtained with a medical imaging technique and at least one clinical and/or biological data previously obtained from the subject;

calculating a score of fat infiltration heterogeneity on the at least one image, said score of fat infiltration being calculated based on at least one radiomic feature obtained for a region of interest (ROI) defined on the at least one image so as to comprise at least one skeletal muscle, wherein the at least one radiomic feature is the energy;

combining the calculated score of fat infiltration heterogeneity with the at least one clinical and/or biological data previously obtained from the subject;

determining a risk for the subject of having or developing steatohepatitis and/or a complication thereof based on the combination of the calculated score of fat infiltration heterogeneity with the at least one clinical and/or biological data.

According to one embodiment, the steatohepatitis is non-alcoholic steatohepatitis (NASH).

According to one embodiment, the step of combining the calculated score of fat infiltration heterogeneity with the at least one clinical and/or biological data of the subject comprises using a machine learning model.

According to one embodiment, the score of fat infiltration is calculated based on the energy and at least one other radiomic feature.

According to one embodiment, the at least one other radiomic feature is a first-order gray level statistics obtained from the image pixels or at least one area of the image.

According to one embodiment, the at least one other radiomic feature is selected from mean absolute deviation, root mean square, uniformity, minimum intensity, maximum intensity, mean intensity, median, intensity range, intensity variance, intensity standard deviation, skewness, kurtosis, variance and entropy.

According to one embodiment, the at least one other radiomic feature is a second-order gray level statistics obtained from cooccurrence matrices of the image, said second-order gray level statistics being selected from contrast, correlation between neighboring image areas or pixels, energy, homogeneity first type, homogeneity second type, inverse difference moment, sum average, sum variance, sum entropy, autocorrelation, cluster prominence, cluster shade, cluster tendency, dissimilarity, normalized inverse difference moment, normalized inverse difference, inverse variance; run-length gray level statistics, short run emphasis, long run emphasis, run percentage, gray-level non-uniformity, run length non-uniformity, low gray level run emphasis, high gray level run emphasis, shape and size based features, such as perimeter, cross-sectional area, major axis length, maximum diameter, and volume; gray-level size-zone matrix based features, such as small area emphasis, large area emphasis, intensity variability, size-zone variability, zone percentage, low intensity emphasis, high intensity emphasis, low intensity small area emphasis, high intensity small area emphasis, low intensity large area emphasis, and high intensity large area emphasis. In one embodiment, the second-order gray level statistics contains different features subgroups, such as Gray-Level Cooccurrence Matrix (GLCM), Gray-Level Run-length Matrix (GLRLM), Gray-Level Size Zone Matrix (GLSZM) and Gray-Level Distance Zone Matrix (GLDZM), Neighborhood Gray-Tone Difference Matrix (NGTDM) or Neighborhood Gray-Level Dependence Matrix (NGLDM).

According to one embodiment, the score of fat infiltration heterogeneity is a function of the energy and at least one other radiomic feature, each one weighted by a weighting factor.

According to one embodiment, the at least one clinical and/or biological data is selected from age, sex, and personal or familial history of metabolic-associated adverse events.

According to one embodiment, the machine learning model is a random forest.

According to one embodiment, the complication of steatohepatitis is selected from hepatocellular carcinoma (HCC), fibrosis (e.g. liver fibrosis), cirrhosis, and cardiovascular diseases.

According to one embodiment, the subject suffers from dysmetabolic status, obesity, metabolic syndrome, overweightness, and/or fatty liver disease, in particular non-alcoholic fatty liver disease (NAFLD).

According to one embodiment, the subject suffers from NASH.

According to one embodiment, the medical imaging technique is computed tomography, magnetic resonance imaging or ultrasounds.

The present invention further relates to a device for determining a risk of having or developing steatohepatitis (NASH) and/or a complication thereof in a subject, said device comprising:

at least one input configured to receive at least one image of the subject previously obtained with a medical imaging technique and at least one clinical and/or biological data previously obtained from the subject;

at least one processor configured to:

calculate a score of fat infiltration heterogeneity on the at least one image, said score of fat infiltration being calculated based on at least one radiomic feature obtained for a region of interest defined on the at least one image so as to comprise at least one skeletal muscle, wherein the at least one radiomic feature is the energy;

combine the calculated score of fat infiltration heterogeneity with the at least one clinical and/or biological data previously obtained from the subject;

determining a risk for the subject of having or developing NASH and/or a complication thereof based on the combination of the calculated score of fat infiltration heterogeneity with the at least one clinical and/or biological data;

at least one output adapted to provide said risk.

The device for determining a risk may be implemented in various ways with proper associated user interface, whether together or separately, notably as a standalone software installed in a computer, a cloud-based service or an Application Programming Interface (API).

A computer program comprising software code adapted to perform a method for predicting a risk of having or developing steatohepatitis (NASH) and/or a complication thereof in a subject according to any one of the embodiments described hereabove when it is executed by a processor.

In addition, the disclosure relates to a computer program comprising software code adapted to perform a method for determining a risk compliant with any of the above execution modes when the program is executed by a processor.

The present disclosure further pertains to a non-transitory program storage device, readable by a computer, tangibly embodying a program of instructions executable by the computer to perform a method for determining a risk, compliant with the present disclosure.

Such a non-transitory program storage device can be, without limitation, an electronic, magnetic, optical, electromagnetic, infrared, or semiconductor device, or any suitable combination of the foregoing. It is to be appreciated that the following, while providing more specific examples, is merely an illustrative and not exhaustive listing as readily appreciated by one of ordinary skill in the art: a portable computer diskette, a hard disk, a ROM, an EPROM (Erasable Programmable ROM) or a Flash memory, a portable CD-ROM (Compact-Disc ROM).

Definitions

In the present invention, the following terms have the following meanings:

The terms "adapted" and "configured" are used in the present disclosure as broadly encompassing initial configuration, later adaptation or complementation of the present device, or any combination thereof alike, whether effected through material or software means (including firmware).

The term "processor" should not be construed to be restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g. an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

An "image" concerns a visual representation of a scene, presently including at least a portion of the subject comprising at least one skeletal muscle at a given point of time. Accordingly, the image may possibly be a frame or a set of frames.

"Image segmentation" consists in partitioning a digital image into multiple segments by assigning labels to image pixels, with a view to easier following processing.

"Machine learning (ML)" designates in a traditional way computer algorithms improving automatically through experience, on the ground of training data enabling to adjust parameters of computer models through gap reductions between expected outputs extracted from the training data and evaluated outputs computed by the computer models.

"Datasets" are collections of data used to build an ML mathematical model, so as to make data-driven predictions or decisions. In "supervised learning" (i.e., inferring functions from known input-output examples in the form of labelled training data), three types of ML datasets (also designated as ML sets) are typically dedicated to three respective kinds of tasks: "training", i.e., fitting the parameters, "validation", i.e., tuning ML hyperparameters (which are parameters used to control the learning process), and "testing", i.e., checking independently of a training dataset exploited for building a mathematical model that the latter model provides satisfying results.

"Radiomic feature" refers to a feature extracted from radiographic medical images using data-characterization algorithms. The concept of radiomics is based on the assumption that biomedical images contain information of disease-specific processes that are imperceptible by the human eye and thus not accessible through traditional visual inspection of the generated images. Through mathematical extraction of the spatial distribution of signal intensities and pixel interrelationships, radiomics quantifies textural information. In addition, visual appreciable differences in image intensity, shape, or texture can be quantified by means of radiomics, thus overcoming the subjective nature of image interpretation. Thus, radiomics does not imply any automation of the diagnostic processes, rather it provides existing ones with additional data.

The radiomics or intensity-based statistical features describe how intensities within the region of interest (ROI) are distributed. The set of intensities of the Nv voxels included in the ROI intensity mask is denoted as $X_{gl} = \{X_{gl,1}, X_{gl,2}, \ldots, X_{gl,Nv}\}$. An intensity histogram can be generated by discretising the original intensity distribution $X_{gl}$ into intensity bins. Let $X_d = \{X_{d,1}, X_{d,2}, \ldots, X_{d,Nv}\}$ be the set of Ng discretised intensities of the $N_v$ voxels in the ROI intensity mask. Let $H = \{n1, n2, \ldots, n_{Ng}\}$ be the histogram with frequency count $n_i$ of each discretised intensity i in $X_d$. The occurrence probability $p_i$ for each discretised intensity i is then approximated as $p_i = n_i/N_v$. The mean $\mu$ and standard deviation $\sigma$ of grey levels of voxels assigned to the ROI are calculated. For example, "Energy" refers to a radiomic feature calculated as follows $$\sum_{i=1}^{N_g} p_i^2.$$

"Entropy" refers to a radiomic feature calculated as follows $$-\sum_{i=1}^{N_g} p_i \log_2 p_i.$$

"Skewness" refers to a radiomic feature calculated as follows $$\frac{\sum_{i=1}^{N_g} (i-\mu)^3 p_i}{\left(\sum_{i=1}^{N_g} (i-\mu)^2 p_i\right)^{3/2}}.$$

"Kurtosis" refers to a radiomic feature calculated as follows $$\frac{\sum_{i=1}^{N_g} (i-\mu)^4 p_i}{\left(\sum_{i=1}^{N_g} (i-\mu)^2 p_i\right)^2} - 3.$$

"Variance" refers to a radiomic feature calculated as follows $$\sum_{i=1}^{N_g} (i-\mu)^2 p_i.$$

Image input for radiomics calculation can be a raw medical image or a medical image preprocessed with techniques mastered by one skilled in the art, such as grey value discretization or intensity-outlier filtering.

"Biological data" refers to a parameter that may be measured in a sample obtained from the subject. For example, said parameter may be measured in a blood, plasma, or serum sample obtained from the subject by means of a commonly used laboratory test. Blood sugar (also referred to as blood glucose or glycemia), cholesterol, high-density lipoprotein (HDL), low-density lipoprotein (LDL), alanine aminotransferase (ALT), and aspartate aminotransferase (AST) are non-limitative examples of biological data.

"Clinical data" refers to a data recovered from external observation of the subject, without the use of laboratory tests. Age (Age), ethnicity (Race), gender (Sex), diastolic blood pressure (DBP) and systolic blood pressure (SBP), family history (FamHX), height (HT), weight (WT), waist (Waist) and hip (Hip) circumference, body-mass index (BMI) are non-limitative examples of clinical data.

"AUROC" stands for area under the ROC curve, and is an indicator of the accuracy of a diagnostic test. In statistics, a receiver operating characteristic (ROC), or ROC curve, is a graphical plot that illustrates the performance of a binary classifier system as its discrimination threshold is varied. The curve is created by plotting the sensitivity against the specificity (usually 1-specificity) at successive values from 0 to 1. ROC curve and AUROC are well-known in the field of statistics (i.e., it tells how much the model is capable of distinguishing between classes).

"NAFLD" (non-alcoholic fatty liver disease) is characterized by the presence of hepatic steatosis, said steatosis developing in the absence of significant alcohol consumption, use of steatogenic medication or hereditary disorders or inborn error of metabolism. NAFLD includes different stages of severity of the disease, a stage less severe, the NAFL (non-alcoholic fatty liver), and a more severe stage, the NASH (non-alcoholic steatohepatitis).

"NASH" (non-alcoholic steatohepatitis) refers to the presence of a score≥1 for each of the three components of the NAS: steatosis, lobular inflammation and ballooning with or without fibrosis.

"Risk" in the context of the present invention, relates to the probability that an event will occur over a specific time period (e.g. 0, 1, 2, 3, 4, 5, 6, 7, 8, 9, 10, 11 or 12 months, or 2 to 7 years), and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed.

"Score" refers to any digit value obtained by the mathematical combination of markers. In one embodiment, a score is a bound digit value, obtained by a mathematical function. In one embodiment, the score may range from 0 to 1.

"Sensitivity", for a diagnostic test, measures the proportion of patients with the diagnostic target that are correctly identified as such (i.e., the percentage of patients with the diagnostic target who are correctly identified by a positive diagnostic test).

"Specificity", for a diagnostic test, measures the proportion of patients without the diagnostic target that are correctly identified as such (i.e., the percentage of patients without the diagnostic target who are correctly identified by a negative diagnostic test).

"Steatosis" refers to the accumulation of fat into the liver as lipid droplets within hepatocytes.

"Steatohepatitis" refers to a metabolic dysfunction-associated fatty liver disease mainly characterized by liver inflammation, hepatocellular injury and fat accumulation into the liver.

"Subject" refers to a mammal, preferably a human.

"Skeletal muscle" refers to voluntary muscles which are under the control of the somatic nervous system.

"Complication" or "complication thereof" refers to an adverse event that is associated with steatohepatitis, in particular NASH, or to the progression of steatohepatitis, in particular NASH in the subject. Steatohepatitis complications are for example, fibrosis (e.g. liver fibrosis), cirrhosis, hepatocellular carcinoma (HCC) and cardiovascular diseases.

"Energy" is a measure of the magnitude of voxel values in an image. This is a measure of the homogeneity of the image array. A larger value implies a greater sum of the squares of these values hence reflects on a greater homogeneity or a smaller range of discrete intensity values. This feature is volume-confounded.

"Entropy" specifies the uncertainty/randomness in the image values. It measures the average amount of information required to encode the image values.

"Skewness" measures the asymmetry of the distribution of values about the Mean value. Depending on where the tail is elongated and the mass of the distribution is concentrated, this value can be positive or negative.

"Kurtosis" is a measure of the 'peakedness' of the distribution of values in the image ROI. A higher kurtosis implies that the mass of the distribution is concentrated towards the tail(s) rather than towards the mean. A lower kurtosis implies the reverse: that the mass of the distribution is concentrated towards a spike near the Mean value.

"Variance" is the mean of the squared distances of each intensity value from the Mean value. This is a measure of the spread of the distribution about the mean.

"Fibrosis", in the present invention, specifically refers to liver fibrosis, a pathological lesion of the liver made of scar tissue including fibrillary proteins or glycoproteins (collagens, proteoglycans . . . ).

"NAFLD Activity Score (NAS)" refers to a system of scoring the histological features of nonalcoholic fatty liver disease (NAFLD). The NAS ranges from 0 to 8, and corresponds to the sum of the scores for steatosis, lobular inflammation and ballooning. The NAS scoring system is commonly used for the histological diagnosis of NASH, defined as the presence of a score≥1 for each of the three components of the NAS. In one embodiment, a NAS score≥4 defines an active NASH. In one embodiment, a NAS score<3 defines an inactive NASH.

"NAFLD Fibrosis Score" is an algorithm that estimates the amount of scarring in the liver. The algorithm is based on 6 clinical and laboratory tests, namely, age, body mass index, impaired fasting blood glucose or presence of diabetes, aspartate aminotransferase (AST) to alanine aminotransferase (ALT) ratio, Blood platelet count and serum albumin concentration.

"Histological inflammation Score" is a score based on the grading of inflammation seen at the histological examination of a liver specimen (i.e., a liver biopsy). It is characterized according to severity (absent, mild, moderate, severe) that refers to the number of foci of inflammatory cells per microscopic high power field and to location within the liver lobule.

BRIEF DESCRIPTION OF THE DRAWINGS

FIG. 3 is a table representing the demographic and histological characteristics of NAFLD population.

FIG. 4 is a table showing that myosteatosis degree is higher in NAFLD patients with HCC than in those without HCC.

FIG. 5 is a table showing that HCC is a significant predictor of myosteatosis degree in patients with NAFLD.

FIG. 6 is a table showing that myosteatosis is strongly associated with NASH related-HCC independently from sex, age, gender, visceral fat, NASH activity and fibrosis severity.

FIG. 8 shows that HCC is associated with severe myosteatosis in patients with NASH which measure the quantity of fat in three muscles illustrating the heterogeneity of fat infiltration.

FIG. 10 is a table showing that HCC prevalence is not explained by fibrosis severity in this NAFLD cohort.

FIG. 11 is a table showing that myosteatosis is specifically associated with HCC in NAFLD patients.

FIG. 12 is a table showing increased Erector spinae PDFF associates with a higher risk of HCC in patients with NASH.

FIG. 18 includes graphs a, b, and c showing that the NAFLD fibrosis score is correlated with erector spinae muscle energy, kurtosis and entropy.

FIG. 19 includes graphs a, b, c, and d showing that the NAFLD activity score (NAS) is correlated with leg skewness and that histological inflammation score is correlated with leg skewness and energy as well as psoas skewness.

DETAILED DESCRIPTION

The present description illustrates the principles of the present disclosure. It will thus be appreciated that those skilled in the art will be able to devise various arrangements that, although not explicitly described or shown herein, embody the principles of the disclosure and are included within its scope.

All examples and conditional language recited herein are intended for educational purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein may represent conceptual views of illustrative circuitry embodying the principles of the disclosure. Similarly, it will be appreciated that any flow charts, flow diagrams, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, a single shared processor, or a plurality of individual processors, some of which may be shared.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

Figure 1:
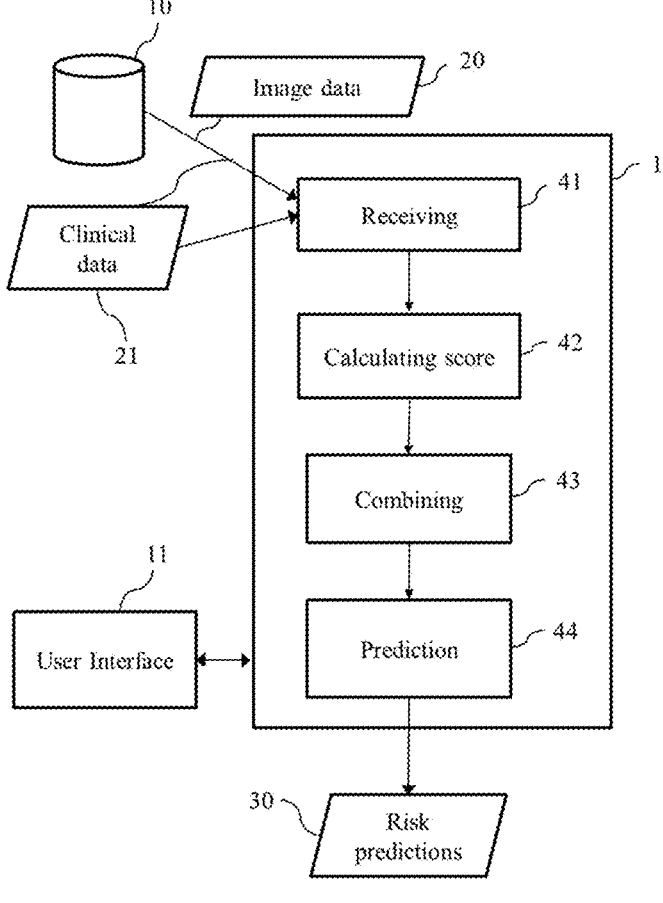
FIG. 1 is a block diagram representing schematically a particular mode of a device for predicting a risk of developing non-alcoholic steatohepatitis (NASH) and/or a complication thereof, compliant with the present disclosure.

The present disclosure will be described in reference to a particular functional embodiment of a device 1 for determining a risk of having or developing steatohepatitis, in particular non-alcoholic steatohepatitis (NASH), and/or a complication thereof in a subject, as illustrated on FIG. 1.

The device 1 is adapted to produce such risk predictions 30 for the subject of having or developing steatohepatitis, in particular NASH, and/or a complication thereof based on image data 20 representative of fat infiltration heterogeneity in skeletal muscles and clinical and/or biological data 21 related to the subject The at least one image of the subject 20 may be derived using a medical imaging technique such as computed tomography, magnetic resonance imaging or ultrasounds. The images may be grayscale images or color images. The image data 21 may include numerical data, such as digital data. Those data may include individual image data in a compressed form, as well known to a person skilled in image compression, such as e.g. in compliance with JPEG (for Joint Photographic Experts Group), JPEG 2000, DICOM or HEIF (for High Efficiency Image File Format) standard. The image includes individual image data in a compressed form recognized by Digital Imaging and Communication in Medicine (DICOM).

The present invention thus further relates to a method for determining a risk of having or developing steatohepatitis, in particular NASH, and/or a complication thereof in a subject, wherein said method comprises the use of the device 1 as described herein.

In one embodiment, the method is a method for assessing whether a subject is at risk of having or developing steatohepatitis, in particular NASH, and/or a complication thereof in a subject.

In one embodiment, the method is a method for diagnosing a steatohepatitis, in particular NASH, and/or a complication thereof in a subject, i.e., for determining if said subject is affected with steatohepatitis, in particular NASH, and/or with a complication thereof.

In one embodiment, the method is a method for predicting whether a subject is at risk of developing steatohepatitis, in particular NASH; and/or a complication thereof in a subject. In one embodiment, the method is for determining, for a subject, a risk of developing steatohepatitis, in particular NASH, and/or a complication thereof in a subject in the future, such as, for example, over a period of time of 2, 3, 4, 5, 6, 7, 8, 9, 10 or 11 months or in the next year or next two to seven years.

In one embodiment, the method is for assessing the presence and/or severity of NAFLD. In one embodiment the severity of NAFLD is assessed by a fibrosis score, the NAFLD activity score (NAS) and/or the histological inflammation score. A fibrosis score estimates liver fibrosis in patients with NAFLD. The fibrosis score includes six variables: age, hyperglycemia, body mass index, platelet count, albumin and AST/ALT ratio). The NAS comprises the measurement of the score of three parameters: lobular inflammation, hepatocellular ballooning and fibrosis. The NAS scoring system is commonly used for assessing the severity of NAFLD and the histological diagnosis of NASH, defined as the presence of a score$\geq$1 for each of the three components of the NAS. In one embodiment, a NAS score$\geq$4 defines an active NASH. In one embodiment, a NAS score$<$3 defines an inactive NASH. In one embodiment, clinically-relevant definitions of steatohepatitis are subject to constant evolution/improvement and could be defined in the future based on pattern detected by machine learning algorithms.

In one embodiment, the method is for determining, in a subject not affected with steatohepatitis, in particular NASH, a risk of developing steatohepatitis, in particular NASH.

In one embodiment, the method is for determining, in a subject affected with a non-complicated NASH, a risk of developing a complication of NASH. In one embodiment, the method is for determining, in a subject affected with NASH, a risk of developing a complication of NASH.

In one embodiment, the method is for diagnosing NASH in a subject, and for determining a risk of developing a NASH complication.

The present invention further relates to a method for providing an adapted care to a subject at risk of having or developing steatohepatitis, in particular NASH, and/or a complication thereof, wherein said method comprises the step of:

determining for the subject a risk of having or developing steatohepatitis, in particular NASH, and/or a complication thereof in a subject using the method as described herein, and providing an adapted care to said subject.

In one embodiment, the subject is at risk of having or developing steatohepatitis, in particular NASH and/or a complication thereof, and an adapted care may comprise, for example, monitoring the subject for the development of steatohepatitis, in particular NASH or complication thereof, such as, for example, by repeating the method for determining a risk of having or developing NASH and/or complication thereof after 0, 1, 2, 3, 4, 5, 6 or 7 months.

In one embodiment, the subject is at risk of having or developing NASH and/or a complication thereof, and an adapted care may comprise, for example, administering a treatment for treating NASH or for treating the complication of NASH to the subject.

According to one embodiment, the method of the invention comprises receiving clinical and/or biological data 21 to combine them with the calculated score of fat infiltration heterogeneity.

The clinical and/or biological data 21, which are as well previously obtained from the subject, may comprise information collected independently of the image data 20, such as information about age, sex, biological data and personal or familial history of metabolic-associated adverse events. These data could be retrieved from a medical database. Other non-limitative examples of clinical data include, but are not limited to, ethnicity, diastolic blood pressure, and systolic blood pressure, height, weight, waist and hip circumference, and body-mass index.

In one embodiment, the method of the invention further comprises a step of comparing the combination of the calculated score of fat infiltration heterogeneity with at least one clinical and/or biological data 21 to a reference value.

In one embodiment, the reference value corresponds to the calculated score of fat infiltration heterogeneity with the at least one clinical and/or biological data 21 measured in a reference population. In one embodiment, the reference value is derived from population studies, including, for example, subjects having a similar age range, or subjects in the same or similar ethnic group.

According to one embodiment, the reference value is derived from the measure of the calculated score of fat infiltration heterogeneity with at least one clinical and/or biological data from one or more subjects who are substantially healthy. In one embodiment, a "substantially healthy subject" is a subject who has not been diagnosed with steatohepatitis, in particular NASH, or a complication thereof. In one embodiment, a "substantially healthy subject" is a subject who has not been diagnosed or identified as having a risk of having or developing steatohepatitis, in particular NASH, or a complication thereof.

According to one embodiment, the reference value is derived from the measure of the calculated score of fat infiltration heterogeneity with at least one clinical and/or biological data from one or more subjects who are diagnosed with steatohepatitis, in particular NASH, and/or with a complication of steatohepatitis, in particular NASH. In one embodiment, the reference value is derived from the measure of the calculated score of fat infiltration heterogeneity with at least one clinical and/or biological data from one or more subjects who were previously determined as at risk of developing steatohepatitis, in particular NASH, and/or with a complication of steatohepatitis, in particular NASH.

The device 1 for predicting is associated with a device for training suited to setting machine learning model parameters of the device 1 in a proper way which will be subsequently described.

Though the presently described device 1 and the device for training are versatile and provided with several functions that can be carried out alternatively or in any cumulative way, other implementations within the scope of the present disclosure include devices having only parts of the present functionalities.

Each of the device 1 and the device for training is advantageously an apparatus, or a physical part of an apparatus, designed, configured and/or adapted for performing the mentioned functions and produce the mentioned effects or results. In alternative implementations, any of the device 1 and the device for training is embodied as a set of apparatus or physical parts of apparatus, whether grouped in a same machine or in different, possibly remote, machines. The device 1 and/or the device for training may e.g. have functions distributed over a cloud infrastructure and be available to users as a cloud-based service, or have remote functions accessible through an API.

The device 1 for predicting and the device for training may be integrated in a same apparatus or set of apparatus, and intended to same users. In other implementations, the structure of the device for training may be completely independent of the structure of device 1, and may be provided for other users. For example, the device 1 may have a parameterized model available to operators for risk predictions, wholly set from previous training effected upstream by other players with the device for training.

In what follows, the modules are to be understood as functional entities rather than material, physically distinct, components. They can consequently be embodied either as grouped together in a same tangible and concrete component, or distributed into several such components. Also, each of those modules is possibly itself shared between at least two physical components. In addition, the modules are implemented in hardware, software, firmware, or any mixed form thereof as well. They are preferably embodied within at least one processor of the device 1 or of the device for training.

The device 1 comprises a receiving module 41 for receiving the at least one image (i.e., image data) of the subject 20 and the at least one clinical and/or biological data 21, as well as ML (machine learning) parameters of the ML model. The at least one image of the subject 20, the at least one clinical and/or biological data 21 and/or the ML parameters may be stored in one or more local or remote database(s) 10. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk). In advantageous embodiments, the ML parameters have been previously generated by a system including the device for training. Alternatively, the ML parameters are received from a communication network.

The device 1 further comprises optionally a preprocessing module (not represented) for preprocessing the received image data 20 and possibly the clinical and/or biological data 21. The preprocessing module may notably be adapted to standardize the received image data 20 for sake of efficient and reliable processing. It may transform the image data 20, e.g. by image decompression. According to various configurations, the preprocessing module is adapted to execute only part or all of the above functions, in any possible combination, in any manner suited to the following processing stage.

In advantageous modes, the preprocessing module is configured for preprocessing the image data 20 so as to have the images standardized. This may enhance the efficiency of the downstream processing by the device 1. Such a standardization may be particularly useful when exploited images originate from different sources, including possibly different imaging systems.

The standardization is advantageously applied to the image data 20 and to images of training datasets (e.g. by the device for training) in a similar way. Notably, the device 1 may deal with image data coming from a given sort of source, while its parameters result from a training based on image data obtained with different types of sources. Thanks to standardization, differences between sources may then be neutralized or minimized. This may make the device 1 more efficient and reliable.

The device 1 also comprises a calculation module 42 for calculating a score representative of fat infiltration heterogeneity in the at least one skeletal muscle of a subject. It may be observed that the operations by the receiving module 41, the preprocessing module and the calculation module 42 are not necessarily successive in time, and may overlap, proceed in parallel or alternate, in any appropriate manner. For example, new image data may be progressively received over time and preprocessed, while the calculation module 42 is dealing with the previously obtained image data 20. In alternative examples, a batch of image data 20 corresponding to a complete sequence acquisition may be fully received and preprocessed before it is submitted to the calculation module 42.

The calculation module 42 may be configured to apply a segmentation algorithm on the image data 20 so as to segment the at least one skeletal muscle. Alternative, the information concerning the boundaries of the at least one skeletal muscle on the data image may be received as input of the module 42 after being manually delineated by a user. The result of the segmentation or of the manual delineation are used by the module 42 to define a region of interest (ROI) on the image data 20 which comprises the pixels of the image data 20 associated to the at least one skeletal muscle.

The at least one skeletal muscle may be a dorsal muscle or lower limb muscles. Lower limb muscles are notably observed using ultrasound. In one embodiment, the at least one skeletal muscle is selected from the group consisting of psoas, quadratus lumborum, erector spinae, oblique and rectus. In one embodiment, the lower limb may be the leg muscle. In one embodiment, the leg muscle contains multiple muscles selected from the group comprising gastrocnemius, soleus and tibialis anterior.

The calculation module 42 is configured to calculate at least one radiomic feature on the ROI. In one embodiment, the at least one radiomic feature is the energy. Indeed, the energy advantageously allows to describing (in)homogeneity in the ROI. The calculation 42 may as well calculate at least one other radiomic feature a first-order gray level statistics obtained from the image pixels or at least one area of the image. Said other radiomic feature being a first-order gray level statistics may be selected from mean absolute deviation, root mean square, uniformity, minimum intensity, maximum intensity, mean intensity, median, intensity range, intensity variance, intensity standard deviation, skewness, kurtosity, variance and entropy. The advantages of using first-order gray level statistics as radiomics feature is that they describe the distribution of individual voxel values, hence of the distribution of fat infiltration, without concern for spatial relationships.

In one embodiment the at least one other radiomic feature is a second-order gray level statistics obtained from cooccurrence matrices of the image, said second-order gray level statistics being selected from contrast, correlation between neighboring image areas or pixels, energy, homogeneity first type, homogeneity second type, inverse difference moment, sum average, sum variance, sum entropy, autocorrelation, cluster prominence, cluster shade, cluster tendency, dissimilarity, normalized inverse difference moment, normalized inverse difference, inverse variance; run-length gray level statistics, short run emphasis, long run emphasis, run percentage, gray-level non-uniformity, run length non-uniformity, low gray level run emphasis, high gray level run emphasis, shape and size based features, such as perimeter, cross-sectional area, major axis length, maximum diameter, and volume; gray-level size-zone matrix based features, such as small area emphasis, large area emphasis, intensity variability, size-zone variability, zone percentage, low intensity emphasis, high intensity emphasis, low intensity small area emphasis, high intensity small area emphasis, low intensity large area emphasis, and high intensity large area emphasis. The advantages of using second-order gray level statistics as radiomics features is that they provide a measure of the spatial arrangement of the voxel intensities, which parallels the intra-muscle heterogeneity and further refine the characterization of the infiltrative pattern of fat within the skeletal muscles.

The calculation module 42 is as well configured to use the at least one radiomic feature to calculate a score representative of the fat infiltration heterogeneity in the at least one at least one skeletal muscle under investigation. Said score of fat infiltration heterogeneity may be a function of the energy and at least one other radiomic feature, each one weighted by a weighting factor. The weighting factor(s) may have been previously derived and stored in the database 10.

The score representative of the fat infiltration heterogeneity in the at least one skeletal muscle under investigation may be calculated in different ways depending from the risk to determine. In one example, to estimate the risk to have steatohepatitis, the score of fat infiltration heterogeneity may be obtained as the weighted sum of the energy and the skewness; to estimate the risk to have HCC (i.e., one complication) the score of fat infiltration heterogeneity may be obtained as the weighted sum of the energy and the entropy, while to estimate the risk to have cardiovascular disease (i.e., one complication) the score of fat infiltration heterogeneity may be obtained as the weighted sum of the energy and the variance. In this example, the weighting factors are adapted to each radiomic feature and each risk to be calculated. One skilled in the art knows how to select the relevant radiomic features and adapt the weighting factors according to the radiomic feature for a given prediction task.

The device 1 also comprises a combination module 43 configured to combine the calculated score of fat infiltration heterogeneity with the at least one clinical and/or biological data 21 previously obtained from the subject. Said combination may be obtained using a weighted sum wherein the clinical and/or biological data 21 are each weighted for a predefined weighting factor and summed to the calculated score of fat infiltration heterogeneity. The at least one clinical and/or biological data 21 may be the sex and the age of the subject or any other clinical or anthropometrical parameter. One skilled in the art is able to select the relevant clinical and/or biological data 21 and adapt the predefined weighting factors according to the clinical and/or biological data 21 for a given prediction task. Said combination may be performed using a machine learning model which receives as input the score of fat infiltration heterogeneity and the clinical and/or biological data 21. The machine learning model may be chosen from the predictive modelling approaches such as the decision trees or Support Vector Machine. In an advantageous embodiment, a Random Forest or Support Vector Machine or a neural network is used as machine learning model as both are top-performing models in disease-risk prediction. The machine learning model may be trained in a supervised way in the device for training and its performance may be verified using k-fold Cross-validation technique. The machine learning parameters determined during training in the device for training may be stored in the database 10.

The device 1 comprises a determination module 44 configured to determine the risk 30 for the subject of having or developing steatohepatitis, in particular NASH, and/or a complication thereof based on the output of the combination module 43 which combines the calculated score of fat infiltration heterogeneity with the at least one clinical and/or biological data 21. The module 44 may as well output the risk 30.

The module 44 may more precisely provide the risk 30, insofar as sufficient information is available for the image data and clinical and/or biological data. This may take the visual form of a written string of characters or a point on a graph showing the degree of probability that the subject has or will develop steatohepatitis, in particular NASH, or a complication thereof.

The device 1 is interacting with a user interface 11, via which information can be entered and retrieved by a user. The user interface 11 includes any means appropriate for entering or retrieving data, information or instructions, notably visual, tactile and/or audio capacities that can encompass any or several of the following means as well known by a person skilled in the art: a screen, a keyboard, a trackball, a touchpad, a touchscreen, a loudspeaker, a voice recognition system.

According to one embodiment, the subject is a male. In another embodiment, the subject is a female.

According to one embodiment, the subject is an adult. According to the present invention, an adult is a subject above the age of 18, 19, 20 or 21 years. In another embodiment, the subject is a child. According to the present invention, a child is a subject below 21, 20, 19 or 18 years, such as, for example, 17, 16, 15, 14, 13, 12, 11, 10 or 9 years.

According to one embodiment, the subject may be a substantially healthy subject, which means that the subject has not been previously diagnosed or identified as having or suffering from a NAFLD, NAFL or NASH.

According to one embodiment, the subject is a patient, i.e., a warm-blooded animal, more preferably a human, who/which is awaiting the receipt of, or is receiving, medical care or was/is/will be the subject of a medical procedure, or is monitored for the development or progression of a disease. According to one embodiment, the subject is a human patient who is treated and/or monitored for the development or progression of a liver disease or condition (preferably NAFLD, NAFL or NASH).

According to one embodiment, the subject suffers from dysmetabolic status, obesity, metabolic syndrome, overweight, and/or fatty liver disease (in particular NAFLD). In one embodiment, the subject suffers from obesity, metabolic syndrome, overweight, and/or fatty liver disease (in particular NAFLD). According to one embodiment, the subject suffers from steatohepatitis. In embodiment, the subject suffers from NASH. In one embodiment, the method of the present invention is for determining a risk of having or developing a complication of steatohepatitis, in particular NASH, in a subject diagnosed with steatohepatitis, in particular NASH.

According to one embodiment, the complication of steatohepatitis, in particular NASH, is selected from hepatocellular carcinoma (HCC), fibrosis (e.g. liver fibrosis), cirrhosis and cardiovascular diseases. In one embodiment, the cardiovascular disease is selected from atherosclerosis, coronary heart disease, cerebrovascular accident, cardiomyopathy, heart failure, valvular heart disease, and cardiac arrhythmias. In one embodiment, the method of the present invention is thus for determining a risk of having inflammation (e.g. liver inflammation), fibrosis (e.g. liver fibrosis) or cirrhosis or HCC in a subject diagnosed with NASH.

Figure 2:
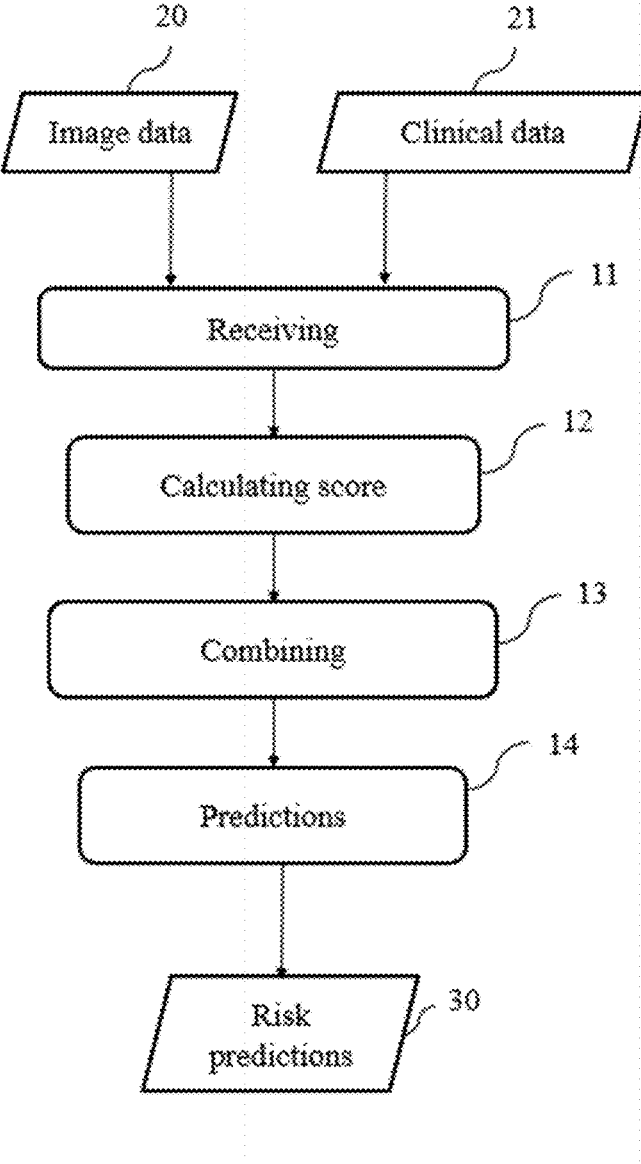
FIG. 2 is a flow chart showing successive steps executed with the device for predicting of FIG. 1.

In its automatic actions, the device 1 may for example execute the following process (FIG. 2):

- receiving the image data 20 and the clinical and/or biological data 21, both previously obtained from the subject (step 11),
- calculating a score of fat infiltration heterogeneity on the at least one image, said score of fat infiltration being calculated based on at least one radiomic feature obtained for a region of interest (ROI) defined on the at least one image so as to comprise at least one skeletal muscle, (step 12),
- combining the calculated score of fat infiltration heterogeneity with the at least one clinical and/or biological data 21 previously obtained from the subject (step 13),
- determining and providing a risk 30 for the subject of having or developing steatohepatitis, in particular NASH, and/or a complication thereof based on the combination of the calculated score of fat infiltration heterogeneity with the at least one clinical and/or biological data (step 14).

A particular apparatus may embody the device 1 as well as the device for training described above. It corresponds for example to a workstation, a laptop, a tablet, a smartphone, or a head-mounted display (HMD).

EXAMPLES

The present invention is further illustrated by the following examples.

Example 1

Materials and Methods

This retrospective study (project N° 2017-030) obtained local IRB approval. Informed consent was waived because of the retrospective nature of the study. Between January 2014 and June 2017, 196 patients with liver biopsy or resection and liver MRI including a multi-echo gradient-echo acquisition sequence within a 4-month interval were included in the study. First, patients with confounding conditions for liver steatosis were excluded (i.e., alcohol intake, chemotherapy, viral infection, etc.). Those with steatofibrosis (i.e., histologically defined as having at-least 1 point in steatosis score, 0 in activity score and ≥F3) or unsatisfactory liver biopsy on MRI were excluded. Finally, acquisitions from 4 patients were used for algorithm adjustments and thus excluded, yielding a total of 72 patients for analysis. (FIG. 3)

Liver histology was based on liver biopsy (n=60) or liver resection (n=12). Indication for liver biopsy/resection was: NAFLD/NASH assessment in 25 patients, focal liver lesion in 47 patients including 15 patients with benign lesions (5 patients with liver hepatocellular adenomas and 10 with focal nodular hyperplasia), and 30 patients with malignant lesions (20 with HCCs, 1 with cholangiocarcinoma and 8 with liver metastases). For each patient, liver steatosis, activity and fibrosis were classified according to the SAF score by an experienced pathologist (VP). Steatosis was assessed by the % of hepatocytes containing intracytoplasmic lipid droplets from S0 to S3: S0: <5%; S1: 5%-33%, S2: 34%-66%, S3: >66%. Activity (from A0 to A4) was calculated by addition of ballooning and lobular inflammation grades. Liver fibrosis was classified as absent (F0), mild (F1, perisinusoidal or periportal), moderate (F2 periportal and perisinusoidal), F3 (bridging fibrosis) and F4 (cirrhosis). NASH was diagnosed with the FLIP algorithm. Diagnosis of HCC as well as tumour characteristics including size and differentiation were retrieved from pathological reports.

All MRI were performed in one institution (Radiology department, Beaujon University Hospital Paris Nord—Clichy, France). The patients had a liver examination on a Philips Ingenia 3T system (Philips, Best, the Netherlands) with a gradient amplitude of 40 mT/m and a 32-channel phase array body coil and multi-transmit parallel radiofrequency (RF) transmission technology. A 3D mDIXON sequence with parallel imaging and sensitivity encoding (SENSE) was used for imaging with the following parameters: repetition time (TR) 10.3187 milliseconds, flip angle (FA) 5°, bandwidth 2653 Hz/pixel, echo times: 1.1520, 2.3020, 3.4520, 4.6020, 5.7520, 6.9020, 8.0520 and 9.2020 milliseconds. Acquisition matrix size was between 176×176×43 and 400×400×61, the transverse in plane spatial resolution was between 1.14 mm and 2.05 mm, and slice thickness was equal to 4 mm. Acquisition duration was 20 seconds. PDFF values were corrected for the effects of T2* relaxation and magnetic susceptibility using the T2*-IDEAL approach.

Figure 7:
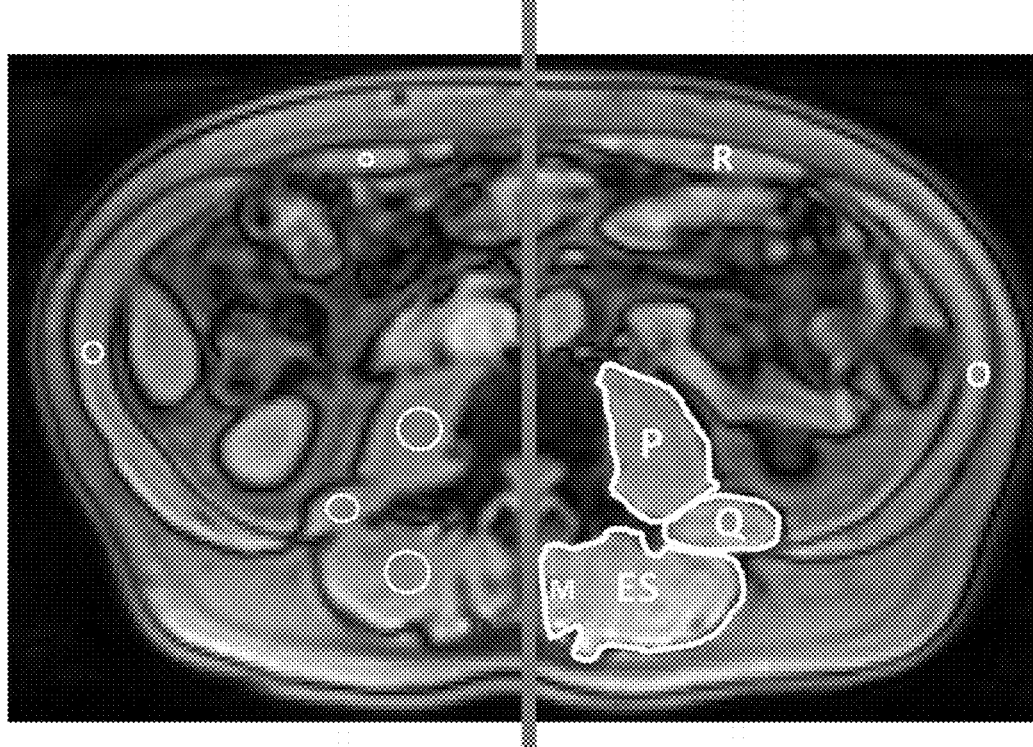
FIG. 7 represents a Magnetic resonance imaging proton density fat fraction (MRI-PDFF) virtual muscle biopsy to evaluate muscle fat concentration at the third lumbar level.

Regions of interest (ROIs) were drawn manually at the third lumbar level in erector spinae (ES), quadratus lumborum, psoas, oblique and rectus muscles bilaterally and mean proton density fat fraction (PDFF), reflecting lipid concentration (%) within each muscle ROI was reported (FIG. 7). These measurements were performed by MN (blinded for liver histology or HCC status) that has previous experience in muscle fat infiltration measurements and following guidelines reported in the orthopedic literature. Two types of ROIs were used: (1) circular ROIs (FIG. 7, left), here after referred to as "virtual muscle biopsy", by carefully placing a circular ROI in the middle of the muscular area avoiding edges, intermuscular adipose tissue and peri-vertebral area and (2) "complete" ROIs (FIG. 7, right) delineated by the muscle anatomical borders. Of note, as per anatomy, in the erector spinae, the "complete" ROIs includes iliocostalis and longissimus as well as multifidus muscle, whereas virtual biopsy excludes multifidus and is thus specific for erector spinae main muscles bundles. Nevertheless, in both cases measures will be referred to as "ES" for simplification. To evaluate inter-observer reliability of virtual biopsy, MN (see above) and MDB (an experienced radiologist) placed ES ROIs in MRI of a subset of patients chosen randomly. Consistency of measurement was excellent (ICC=0.91, 95% CI 0.83-0.95, n=48, p<0.001). The absolute lipid content was computed by multiplying total muscle area (mm²) by the PDFF in the ROI on the same section.

At the same level than that used for muscle analysis, visceral adipose area was measured by MN by drawing a ROI in the zone lining the inner abdominal muscle belt that has a threshold of ≥50% PDFF. Histogram-based radiomic features (first order radiomic features, namely mean, variance, skewness, kurtosis, energy and entropy) were extracted from the 'complete" muscle ROIs with a MAT-LAB algorithm.

All data are presented as mean±standard deviation unless specified otherwise. Statistical analyses were performed using two-tailed Student t-test (equal variance) or Welch t-test (unequal variance), one-way ANOVA followed by Benjamini Hochberg's post-hoc, chi-square test and receiver operating curve (ROC) analysis using Graph Pad Prism 8 software (San Diego, USA). Optimal cut-offs for ROC were determined with Youden's index and corresponding sensitivity and specificity, odds ratio and relative risk computed with Wilson/Brown, Baptista-Pike and Koopman asymptotic score methods, respectively. Multivariate analysis was performed on SPSS v24 (IBM, NY, USA) with multiple linear and binary logistic regressions. Differences were considered significant at values of p<0.05.

Results

Figure 9:
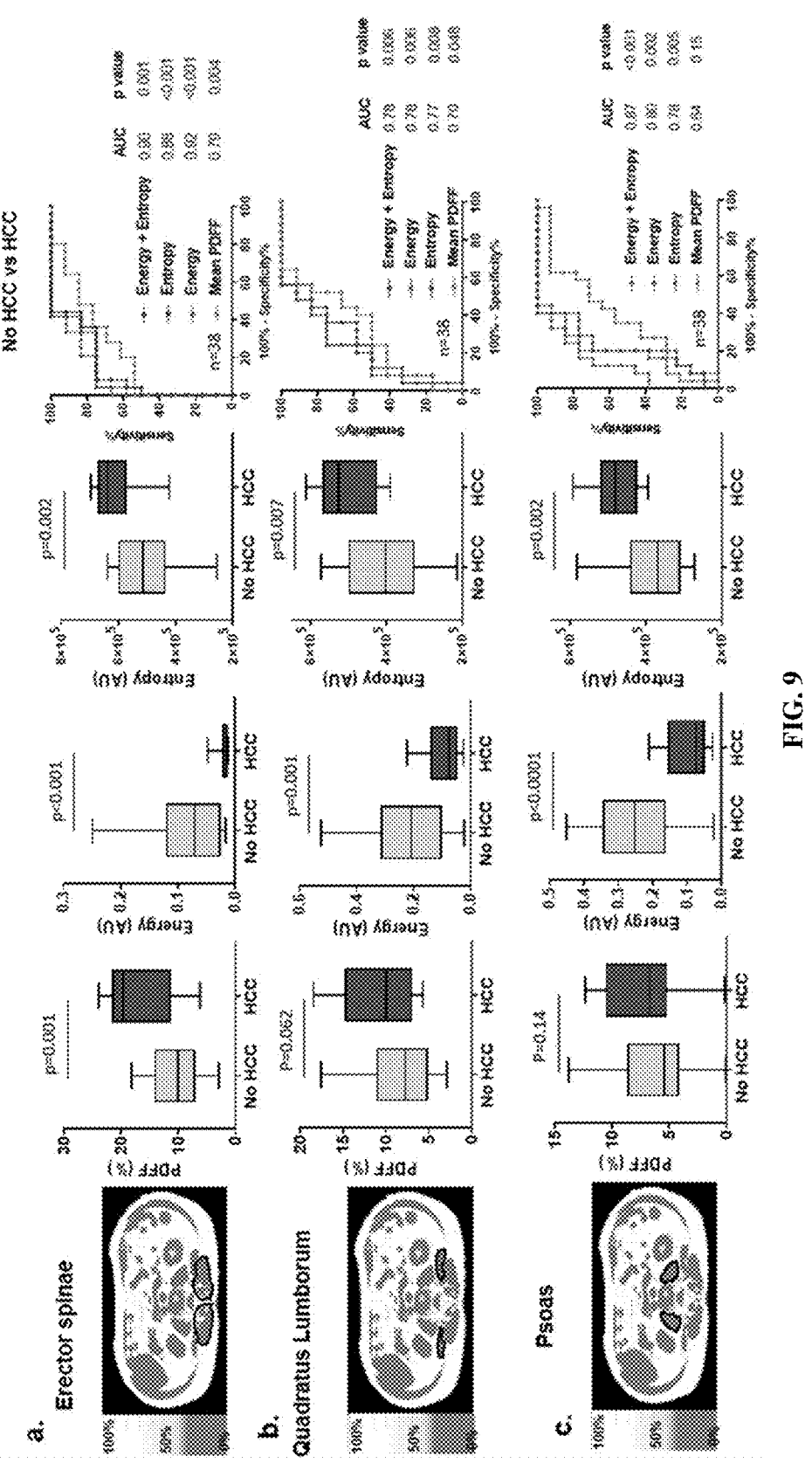
FIG. 9 is a representation of first order radiomics features outperform mean PDFF to predict HCC in patients with NASH.
Figure 13:
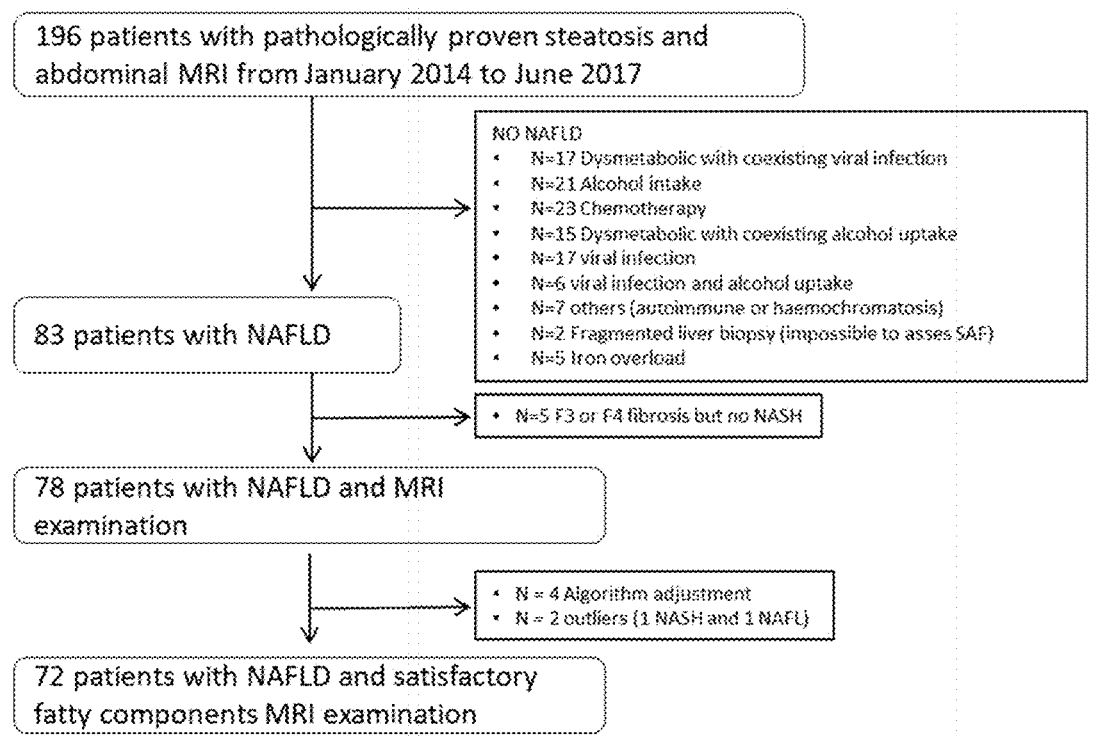
FIG. 13 is flow chart of patients selection.

The total number of patients was 72, with a mean age of 57±14 years and a higher proportion of men (65%, 47/72) (FIG. 9). NASH, as histologically determined by the FLIP algorithm on liver biopsy or resection specimens, was found in 53% of the patients. Forty-five patients had a focal lesion (HCCs 20/45; 44%). HCCs and cirrhosis (F4) were mainly found in patients with NASH (FIG. 9). However, there was no difference in the prevalence of HCC according to fibrosis severity (FIG. 10).

Patients stratified were according to the presence of a focal lesion and its subtype and evaluated muscle fat infiltration with MRI-PDFF-based virtual muscle biopsy. When the focal lesion was diagnosed as HCC, patients had significantly higher PDFF in back muscles (i.e., quadratus lumborum and ES), and particularly in ES, when compared to patients with another type of tumor (i.e., benign, cholangiocarcinoma or metastasis) or without focal lesion (FIG. 11). Muscle PDFF was similar between patients with a benign tumor, a cholangiocarcinoma or liver metastases. Thus, the analysis was resumed considering two groups of patients: those with HCC and those without HCC. Patients with HCC were older than those without HCC (67±9 vs 53±14, p<0.001) and had higher visceral fat area (266±117 cm² vs 202±109 cm²) (FIG. 4). In patients with HCC, MRI-PDFF was significantly higher in dorsal muscles when compared to patients without HCC (4.7±3.6% vs 3.0±2.2% and 9.6±5.5% vs 5.7±3.0%, in quadratus lumborum and ES, respectively, p<0.02). PDFF in other muscles of the abdominal belt (i.e., psoas, oblique and rectus muscle) was not different whether in patients with or without HCC.

Figure 14:
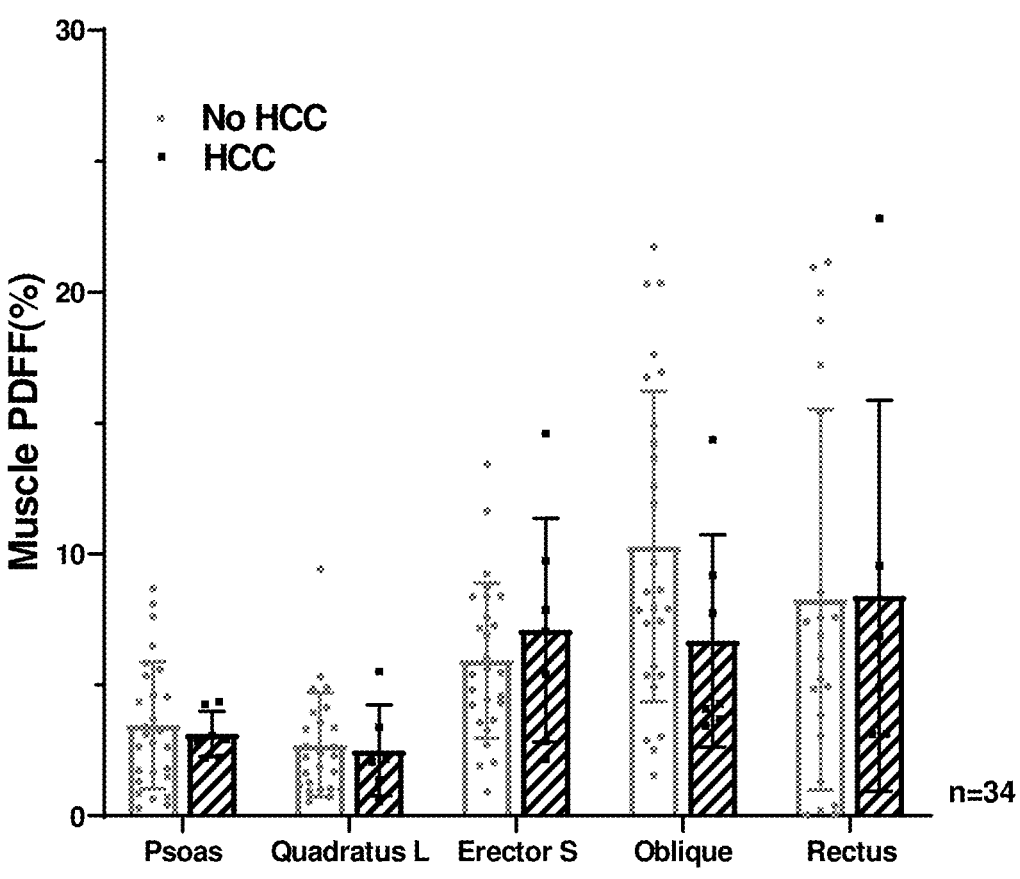
FIG. 14 is a graph showing that HCC is not associated with increased fatty infiltration in patients with NAFL.
Figure 15A:
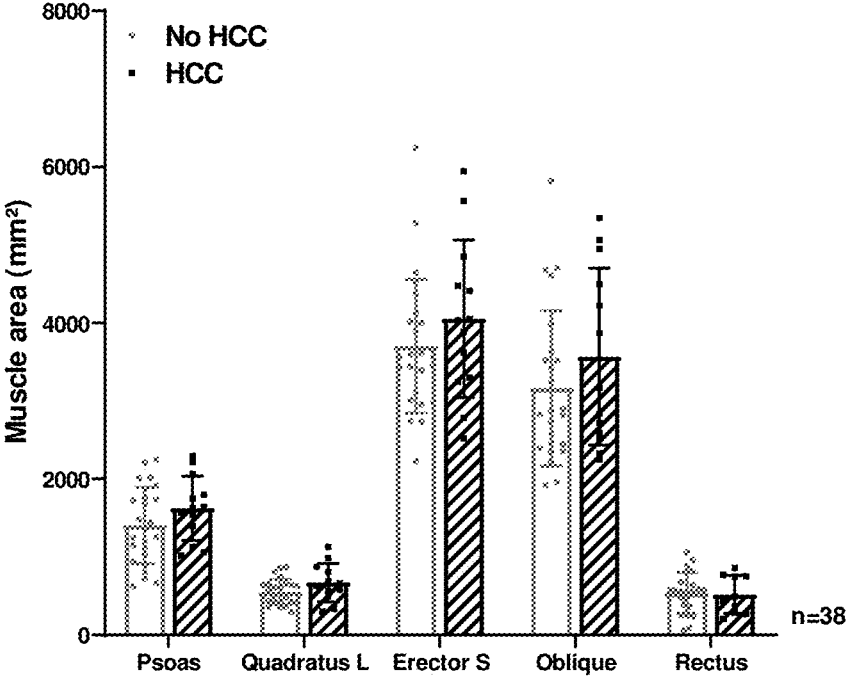
FIGS. 15a and 15b are graphs representing that absolute lipid content is higher in patients with NASH-associated HCC than in those without HCC.
Figure 15B:
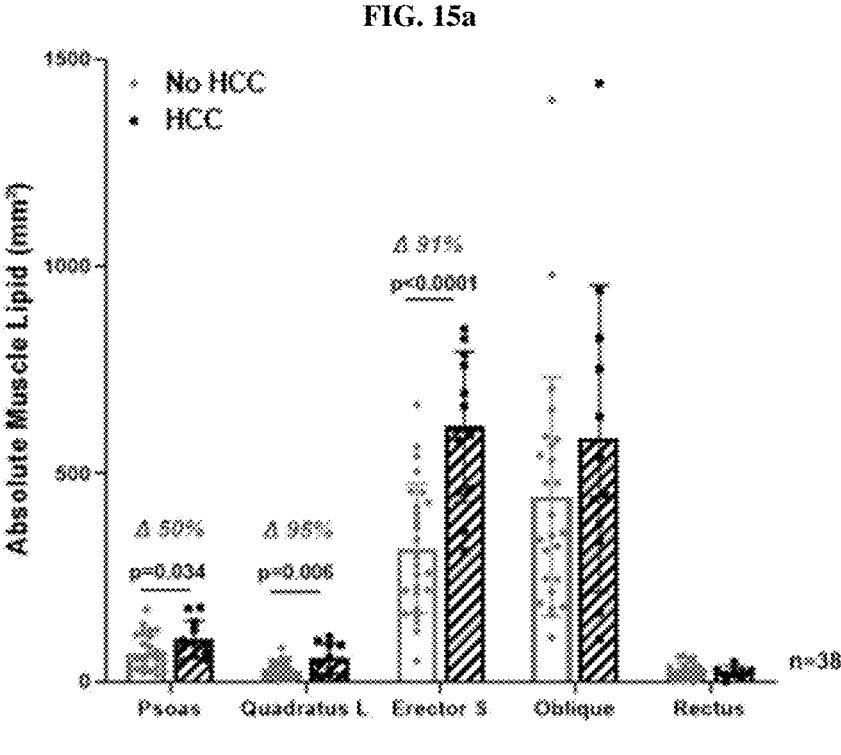

To test whether the NAFLD status influences the relationship between muscle fat infiltration and HCC, patients were stratified according to NASH or not (NAFL) groups (see methods). In the NAFL group, muscle PDFF was similar in patients with or without HCC (FIG. 14). In contrast, in patients with NASH and HCC, muscle fat infiltration was twice as high when compared to patients with NASH but without HCC (11±5% versus 5.4±3.1% in ES) (FIG. 8a-b). ES exhibited the largest difference in PDFF (denoted as ESPDFF) in HCC vs no HCC NASH patients (Δ 103%, p<0.001) and was used as the reference muscle for further analyses. Of note, ES muscle area was comparable between patients with NASH and HCC and those with NASH but without HCC (FIG. 15a). This finding is compatible with a higher total lipid content (and thus a lower lean muscle mass) in patients with NASH and HCC when compared to patients with NASH but without HCC (FIG. 15b).

In addition to HCC, multiple plausible factors such as age, sex, visceral fat area, liver inflammatory activity and fibrosis stage may determine muscle fat infiltration. Therefore, a linear multiple regression model was applied to define the predictors of ESPDFF in the entire cohort (n=72). Age, sex and HCC, but not activity score, fibrosis score or visceral fat area, were significant determinants of ESPDFF in patients with NAFLD.

A multivariate analysis was used to test whether ESPDFF could significantly predict HCC, independently from possible confounding factors. Whether adjusted for age, sex, visceral fat area, liver disease activity (histological score of inflammation and ballooning) and fibrosis stage, ESPDFF remained an independent and significant predictor of HCC in NAFLD patients irrespectively from the model considered (FIG. 6). The association between HCC and ESPDFF was stronger when only the patients with NASH were considered. ROC analysis showed that ESPDFF—whether alone or in combination with the other parameters—predicted with a high performance HCC in patients with NASH (areas under the ROC curves (AUCs): 0.79-0.94, all p<0.05). In patients with NASH, ESPDFF≥9% (Youden index) and ≥10% (optimal specificity) were associated with 2.7 and 6.4 higher relative risk of HCC, respectively (FIG. 12).

Figure 16:
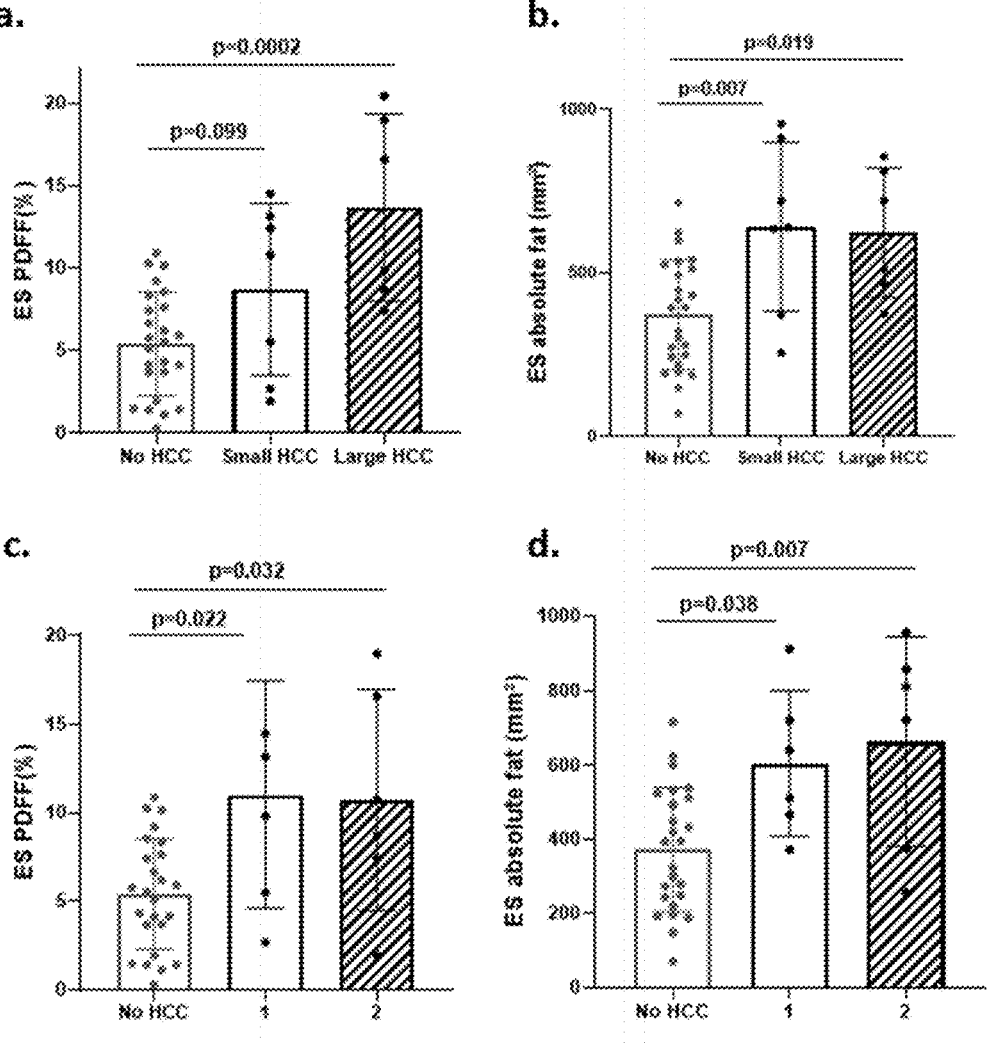
FIG. 16 includes graphs a, b, c, and d showing that muscle fatty infiltration is more severe in patients with NASH and HCC when compared to those without HCC independently from HCC severity.

HCC in patients varied in size and differentiation status. HCC patients were sub-stratified according to HCC size (≥ or <3 cm) or differentiation (well or moderately differentiated). ESPDFF (FIG. 16a, 16c) and ES total lipid content (FIG. 16b, 16d) were not different according to HCC size and pathological differentiation.

Mean PDFF—as measured by virtual liver biopsy—was higher in ES and quadratus lumborum of patients with NASH and HCC when compared to those with NASH but without HCC (FIG. 8). Likewise, when PDFF was measured on whole muscles (i.e., complete ROIs), mean PDFF was higher in ES and quadratus lumborum of patients with NASH and HCC when compared to those with NASH but without HCC (FIG. 9a-c). First order radiomics features were further extracted from complete ROIs (see methods). Muscle energy and entropy (FIG. 9a-c), but not variance, skewness or kurtosis (not shown), had a high power to distinguish between patients with and without HCC. In ES, AUROC of energy and entropy were respectively 0.92 (95% CI 0.82-1.00) and 0.88 (95% CI 0.76-0.99, p<0.0001) to discriminate between patients with and without HCC. Of note, in the NASH population, ESEnergy and ESEntropy were independent predictors of HCC in the multivariate model 3 of the table of FIG. 6 (p=0.047 and p=0.035, ESPDFF excluded). Optimal cut-off for the parameter ESenergy (Youden's index) to discriminate patients with HCC from those without in the NASH population was 0.017, with a sensitivity of 0.96 (95% CI 0.79-0.99) and a specificity of 0.75 (95% CI 0.47-0.91). In addition, the combination of at least one clinical factor (e.g. age and sex) and one first-order radiomic index of skeletal muscles (e.g. energy in erector spinae) shows an AUROC of energy of 0.97 to discriminate between NASH patients with and without HCC (data not shown).

Example 2

Materials and Methods

All measurement is performed as in Example 1, in the psoas muscle instead of the erector spinae. The same group of patients of the example 1 have been used for this example.

Results

Figure 17:
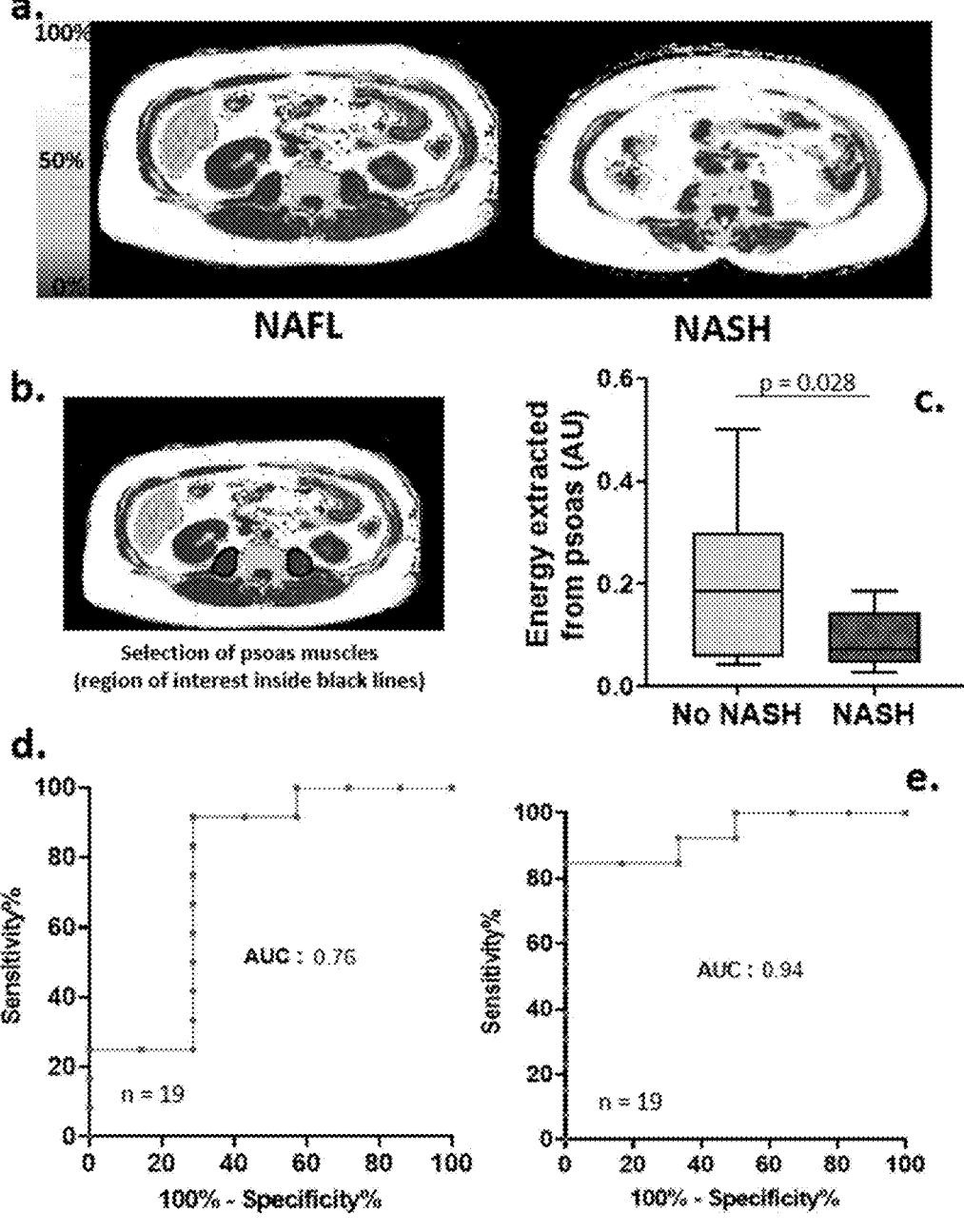
FIG. 17 shows in a, b, c, d, and e that NASH is associated with increase fatty infiltration in comparison to NAFL patients.

In patients with NASH, the heterogeneity of muscle fat infiltration was higher as compared to patients with NAFL patient (FIG. 17a).

First order radiomics features were further extracted from complete ROIs (see methods). As shown in FIGS. 17b and 17c, muscle energy extracted from psoas has a high power to distinguish between patients with and without NASH. In psoas, muscle energy used in a method for discriminating between patients with and without NASH shows an AUROC of 0.76 (FIG. 17d). A machine learning algorithm as described in the present invention (e.g. binary logistic regression) based on the combination of at least one clinical factor (e.g. age and sex) and one first-order radiomic index of skeletal muscles (e.g. energy in psoas), shows an increased AUROC of 0.94 to discriminate between patients with and without NASH (FIG. 17e).

Example 3

Materials and Methods

Patients have been prospectively recruited from the Hepatology outpatients clinic. The inclusion criteria are the following:

Age: 18-75 years

Presence of steatosis as suggested by elevated controlled attenuation parameter (CAP) value on Fibroscan (>252CAP) and/or alanine aminotransferase serum level>25 and >33 in women and men, respectively.

Patients with following criteria have been excluded from the study:

Liver diseases of other etiology: hepatitis B surface antigen or HCV RNA positivity, Wilson's disease, hemochromatosis, a1-antitrypsin deficiency, alcoholic liver disease, etc.

Active IV drug addiction

Previous cirrhosis diagnosis

Pregnant women

Drugs which can cause fatty liver (methotrexate, amiodarone, tamoxifen, oral steroid, etc.)

Active cancer

Significant alcohol consumption

Renal insufficiency

In included patients, we evaluated: body mass, height, history of macro/micro-vascular complications. Fasting blood sample have been performed to measure metabolic parameters (glycaemia, insulinemia, triglyceride and cholesterol profile), CK-18, and liver diseases scores such as Fibrosis-4 (FIB-4) and NAFLD Fibrosis score (NFS).

Muscle radiomics indices have been evaluated non-invasively with MRI-PDFF sequences at the third lumbar level (e.g. to evaluate dorsal muscles) and in the lower limb (e.g. to evaluate leg muscles). Image segmentation and radiomics extraction have been performed with the open-source software the medical imaging interaction toolkit (MITK).

Liver tissue has been collected for histological diagnosis and disease staging and grading according to the NAFLD activity score (NAS). The risk of cardiovascular disease was computed with the SCORE2 risk prediction algorithm.

Results

First order radiomics features were further extracted from complete ROIs. As shown in FIGS. 18a, 18b and 18c, muscle energy, kurtosis and entropy extracted from erector spinae has a high power of correlation with the NAFLD fibrosis score which is indicative of NAFLD severity.

As shown in FIG. 19*a*, there is a strong correlation between muscle radiomic feature skewness in leg muscles and the histological NAFLD activity score (NAS). In addition, the radiomics feature skewness in psoas (FIG. 19*b*) and in leg muscles (FIG. 19*c*), as well as the radiomics feature Energy (FIG. 19*d*), are higher in patients with signs of liver inflammation (histological inflammation score of 1 or 2) when compared to those without signs of liver inflammation.

Figure 20:
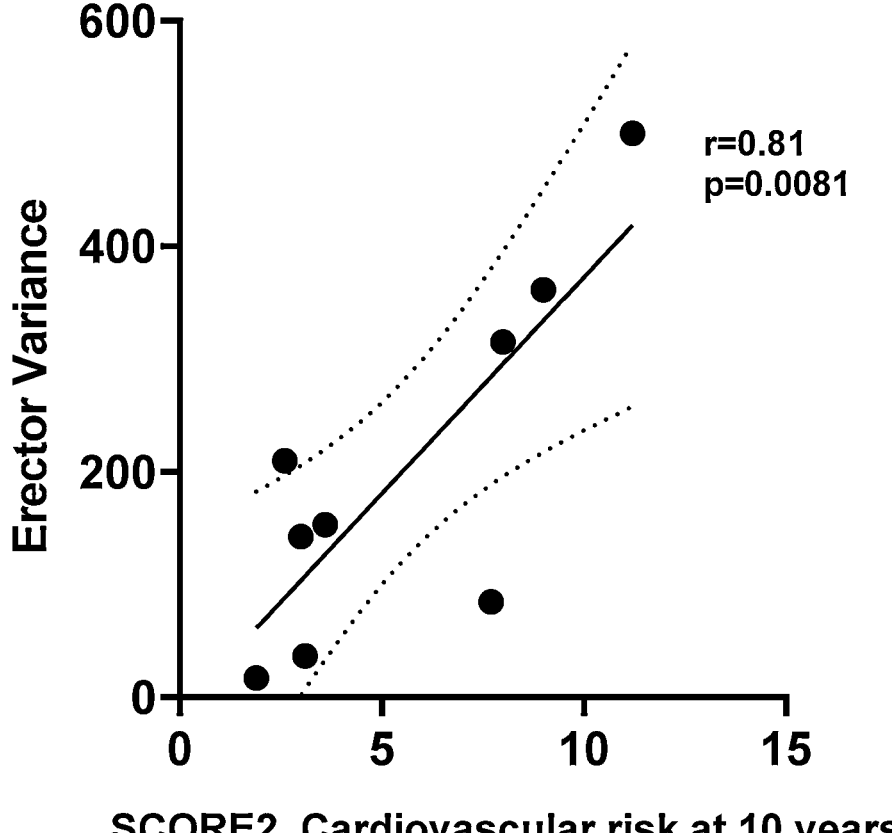
FIG. 20 is a graph showing a correlation between erector spinae variance and the SCORE2 indicative of the risk of cardiovascular disease.

Finally, there is a strong correlation between the muscle radiomic feature variance in the erector spinae muscle and the SCORE2 which is indicative of the risk of cardiovascular disease at 10 years (FIG. 20).

Example 4

Materials and Methods

Patients have been prospectively recruited from the Hepatology outpatients clinic. The inclusion criteria are the following:

Age: 18-75 years

Presence of steatosis as suggested by elevated controlled attenuation parameter (CAP) value on Fibroscan (>252CAP) and/or alanine aminotransferase serum level>25 and >33 in women and men, respectively.

Patients with following criteria have been excluded from the study:

Liver diseases of other etiology: hepatitis B surface antigen or HCV RNA positivity, Wilson's disease, hemochromatosis, a1-antitrypsin deficiency, alcoholic liver disease, etc.

Active IV drug addiction

Previous cirrhosis diagnosis

Pregnant women

Drugs which can cause fatty liver (methotrexate, amiodarone, tamoxifen, oral steroid, etc.)

Active cancer

Significant alcohol consumption

Renal insufficiency

In included patients, we evaluated: body mass, height, history of macro/micro-vascular complications. Fasting blood sample have been performed to measure metabolic parameters (glycaemia, insulinemia, triglyceride and cholesterol profile), CK-18, and liver diseases scores such as Fibrosis-4 (FIB-4) and NAFLD Fibrosis score (NFS).

Muscle radiomics indices have been evaluated non-invasively with MRI-PDFF sequences at the third lumbar level (e.g. to evaluate dorsal muscles) and in the lower limb (e.g. to evaluate leg muscles). Image segmentation and radiomics extraction have been performed with the open-source software the medical imaging interaction toolkit (MITK).

Liver tissue has been collected for histological diagnosis and disease staging and grading according to the NAFLD activity score (NAS). The risk of cardiovascular disease was computed with the SCORE2 risk prediction algorithm.

Results

Different scores are generated in order to predict the risk of having steatohepatitis and/or complications thereof (i.e., HCC and cardiovascular disease).

The score to predict the risk of having steatohepatitis is based on at least one clinical parameter (e.g. age, sex) and at least one radiomic feature (e.g. energy) and at least one other radiomic feature (e.g. variance) in at least one muscle (e.g. erector spinae, leg muscle).

The risk of having steatohepatitis (%) based on leg muscle=101.717 (constant)+0.051*Age−50.569*Sex (0/1)−32.482*Energy (Z-score)+51.792*Skewness (Z-score)+$a_1$*$x_1$+$a_2$*$x_2$+$a_n$*$x_n$.

The score to predict the risk of having one complication of steatohepatitis (e.g. HCC or cardiovascular disease) is based on at least one clinical parameter (e.g. age, sex) and at least one radiomic feature (e.g. energy) and at least one other radiomic feature (e.g. variance).

The risk of having HCC (%) based on erector spinae muscle=−6.661 (constant)+0.08*Age+0.923*Sex (0/1)−0.613*Energy (Z-score)+0.031*Entropy (Z-score)+$a_1$*$x_1$+$a_2$*$x_2$+$a_n$*$x_n$.

The risk of having a cardiovascular disease (%) based on erector spinae muscle=−10.282 (constant)+0.26*Age+2.307*Sex (0/1)+0.735*Energy (Z-score)+0.094*Variance (Z-score)+$a_1$*$x_1$+$a_2$*$x_2$+$a_n$*$x_n$.

In the three scores above, $a_n$ is a continuously evolving coefficient and $x_n$ can be (1) a clinical/anthropometrical/biological parameter, (2) a first- or second-order gray level statistics (radiomics) derived from the muscle of interest or (3) a Z-score normalization of (1) or (2).

The invention claimed is:

1. A computer-implemented method for determining a risk of having or developing steatohepatitis and/or a complication thereof in a subject, said method comprising the steps of:

receiving by a processor device at least one image of the subject previously obtained with a medical imaging technique and at least one clinical and/or biological data previously obtained from the subject;

calculating by the processor device a score of fat infiltration heterogeneity of the at least one image, said score of fat infiltration heterogeneity being calculated based on at least one radiomic feature obtained for a region of interest (ROI) defined in the at least one image to comprise at least one skeletal muscle, wherein the at least one radiomic feature is an energy obtained for the region of interest (ROI);

combining by the processor device the calculated score of fat infiltration heterogeneity with the at least one clinical and/or biological data previously obtained from the subject;

determining by the processor device the risk for the subject having or developing steatohepatitis and/or a complication thereof based on the combination of the calculated score of fat infiltration heterogeneity with the at least one clinical and/or biological data, wherein combining the calculated score of fat infiltration heterogeneity with the at least one clinical and/or biological data of the subject comprises using a machine learning model, wherein the energy obtained for the region of interest (ROI) is calculated as follows $$\sum_{i=1}^{N_g} p_i^2,$$

where $N_g$ stands for a set of discretised intensities of voxels in the ROI, and $p_i$ stands for the occurrence probability for each discretised intensity i, and wherein the method further comprises administering a treatment for treating non-alcoholic fatty liver disease (NAFLD)

or non-alcoholic steatohepatitis (NASH) to the subject having the determined risk that is determined to be above a predetermined risk threshold.

2. The method according to claim 1, wherein the score of fat infiltration heterogeneity is calculated based on the energy obtained for the region of interest (ROI) and at least one other radiomic feature.

3. The method according to claim 2, wherein said at least one other radiomic feature is a first-order gray level statistics obtained from image pixels or at least one area of the at least one image.

4. The method according to claim 3, wherein the at least one other radiomic feature is selected from mean absolute deviation, root mean square, uniformity, minimum intensity, maximum intensity, mean intensity, median, intensity range, intensity variance, intensity standard deviation, skewness, kurtosity, variance and entropy.

5. The method according to claim 2, wherein the at least one other radiomic feature is a second-order gray level statistics obtained from cooccurrence matrices of the at least one image, said second-order gray level statistics being contrast, correlation between neighboring image areas or pixels, energy, homogeneity first type, homogeneity second type, inverse difference moment, sum average, sum variance, sum entropy, autocorrelation, cluster prominence, cluster shade, cluster tendency, dissimilarity, normalized inverse difference moment, normalized inverse difference, inverse variance; run-length gray level statistics, short run emphasis, long run emphasis, run percentage, gray-level non-uniformity, run length nonuniformity, low gray level run emphasis, high gray level run emphasis, shape and size based features; or gray-level size-zone matrix based features.

6. The method according to claim 2, wherein the score of fat infiltration heterogeneity is a function of the energy obtained for the region of interest (ROI) and at least one other radiomic feature, each one weighted by a weighting factor.

7. The method according to claim 1, wherein the at least one clinical data is selected from age, sex, and personal or familial history of metabolic-associated adverse events.

8. The method according to claim 1, wherein the machine learning model is a random forest.

9. The method according to claim 1, wherein the complication of steatohepatitis is selected from hepatocellular carcinoma (HCC), liver fibrosis, cirrhosis, and cardiovascular diseases.

10. The method according to claim 1, wherein the subject suffers from dysmetabolic status, obesity, metabolic syndrome, overweight, and/or fatty liver disease.

11. The method according to claim 10, wherein the subject suffers from nonalcoholic steatohepatitis (NASH) or from non-alcoholic fatty liver disease (NAFLD), and the step of determining by the processor device includes determining the risk for developing a complication thereof.

12. The method according to claim 1, wherein the medical imaging technique is computed tomography, magnetic resonance imaging, and/or ultrasound.

13. The device according to claim 12, wherein the score of fat infiltration heterogeneity is calculated based on the energy obtained for the region of interest (ROI) and at least one other radiomic feature.

14. The device according to claim 13, wherein said at least one other radiomic feature is a first-order gray level statistics obtained from image pixels or at least one area of the at least one image.

15. The device according to claim 14, wherein the at least one other radiomic feature is selected from mean absolute deviation, root mean square, uniformity, minimum intensity, maximum intensity, mean intensity, median, intensity range, intensity variance, intensity standard deviation, skewness, kurtosity, variance and entropy.

16. The device according to claim 13, wherein the at least one other radiomic feature is a second-order gray level statistics obtained from cooccurrence matrices of the at least one image, said second-order gray level statistics being contrast, correlation between neighboring image areas or pixels, energy, homogeneity first type, homogeneity second type, inverse difference moment, sum average, sum variance, sum entropy, autocorrelation, cluster prominence, cluster shade, cluster tendency, dissimilarity, normalized inverse difference moment, normalized inverse difference, inverse variance; run-length gray level statistics, short run emphasis, long run emphasis, run percentage, gray-level non-uniformity, run length nonuniformity, low gray level run emphasis, high gray level run emphasis, shape and size based features; or gray-level size-zone matrix based features.

17. A non-transitory computer-readable storage medium comprising instructions which, when executed by a processor of a computer, cause the computer to carry out the method of claim 1.

18. The method of claim 1, wherein the energy obtained for the region of interest (ROI) is volume-confounded and is a measure of a homogeneity of the image array, wherein a larger value implies a greater homogeneity.

19. The method according to claim 1, further comprising generating the at least one image of the subject with the medical imaging technique and/or generating the at least one clinical and/or biological data from the subject.

20. A system for determining a risk of having or developing steatohepatitis and/or a complication thereof in a subject, said device comprising:

at least one input configured to receive at least one image of the subject previously obtained with a medical imaging technique and at least one clinical and/or biological data previously obtained from the subject; and at least one processor configured to:

calculate a score of fat infiltration heterogeneity of the at least one image, said score of fat infiltration heterogeneity being calculated based on at least one radiomic feature obtained for a region of interest defined in the at least one image to comprise at least one skeletal muscle, wherein the at least one radiomic feature is an energy obtained for the region of interest (ROI);

combine the calculated score of fat infiltration heterogeneity with the at least one clinical and/or biological data previously obtained from the subject;

determine the risk for the subject having or developing steatohepatitis and/or a complication thereof based on the combination of the calculated score of fat infiltration heterogeneity with the at least one clinical and/or biological data;

at least one output adapted to provide said risk, wherein combining the calculated score of fat infiltration heterogeneity with the at least one clinical and/or biological data of the subject comprises using a machine learning model, wherein the energy obtained for the region of interest (ROI) is calculated by the at least one processor as follows $$\sum_{i=1}^{N_g} p_i^2,$$

where $N_g$ stands for a set of discretised intensities of voxels in the ROI, and $p_j$ stands for the occurrence probability for each discretised intensity i, and wherein the at least one processor is further configured to administer or direct administration of a treatment for treating non-alcoholic fatty liver disease (NAFLD) or non-alcoholic steatohepatitis (NASH) to the subject having the determined risk that is determined to be above a predetermined risk threshold.

21. A method for monitoring a response to a treatment in a subject suffering non-alcoholic fatty liver disease (NAFLD) or non-alcoholic steatohepatitis (NASH) and receiving a treatment for the said NAFLD or NASH, said method comprising the steps of:

generating at least one image of the subject previously obtained with a medical imaging technique and at least one clinical and/or biological data previously obtained from the subject;

calculating a score of fat infiltration heterogeneity of the at least one image, said score of fat infiltration being calculated based on at least one radiomic feature obtained for a region of interest (ROI) defined in the at least one image as being one skeletal muscle, wherein the at least one radiomic feature is energy obtained for the region of interest (ROI);

combining the calculated score of fat infiltration heterogeneity with the at least one clinical and/or biological data previously obtained from the subject;

determining a risk for the subject of having or developing a complication from said NAFLD or NASH based on the combination of the calculated score of fat infiltration heterogeneity with the at least one clinical and/or biological data, wherein combining the calculated score of fat infiltration heterogeneity with the at least one clinical and/or biological data of the subject comprises using a machine learning model, wherein the energy obtained for the region of interest (ROI) is calculated as follows $$\sum_{i=1}^{N_g} p_i^2,$$

where $N_g$ stands for a set of discretised intensities of voxels in the ROI, and $p_j$ stands for the occurrence probability for each discretised intensity i, and wherein the method further comprises administering a treatment for treating non-alcoholic fatty liver disease (NAFLD) or non-alcoholic steatohepatitis (NASH) to the subject having the determined risk that is determined to be above a predetermined risk threshold.

* * * * *